(12) United States Patent
Edwards et al.

(10) Patent No.: US 11,590,286 B2
(45) Date of Patent: Feb. 28, 2023

(54) DEVICES, SYSTEMS AND METHODS FOR MEDICAMENT DELIVERY

(71) Applicant: kaleo, Inc., Richmond, VA (US)

(72) Inventors: Eric S. Edwards, Moseley, VA (US); Evan T. Edwards, Charlottesville, VA (US); Mark J. Licata, Doswell, VA (US); Paul F. Meyers, Fishers, IN (US)

(73) Assignee: kaleo, Inc., Richmond, VA (US)

( * ) Notice: Subject to any disclaimer, the term of this patent is extended or adjusted under 35 U.S.C. 154(b) by 749 days.

(21) Appl. No.: 16/554,189

(22) Filed: Aug. 28, 2019

(65) Prior Publication Data
US 2019/0381245 A1 Dec. 19, 2019

Related U.S. Application Data

(60) Division of application No. 16/426,412, filed on May 30, 2019, now Pat. No. 10,737,028, which is a (Continued)

(51) Int. Cl.
*A61M 37/00* (2006.01)
*A61M 5/20* (2006.01)
(Continued)

(52) U.S. Cl.
CPC ............ *A61M 5/2033* (2013.01); *A61M 5/19* (2013.01); *A61M 5/2046* (2013.01);
(Continued)

(58) Field of Classification Search
CPC .... A61M 2005/206; A61M 2005/2073; A61M 5/19; A61M 5/2033; A61M 5/2046; A61M 5/31565; A61M 5/3202; A61M 5/3204
See application file for complete search history.

(56) References Cited

U.S. PATENT DOCUMENTS 2,409,656 A 10/1946 Austin
2,960,087 A 11/1960 Uytenbogaart
(Continued)

FOREIGN PATENT DOCUMENTS

DE 2019296 11/1971
EP 1518575 A1 3/2005
(Continued)

OTHER PUBLICATIONS

Office Action for U.S. Appl. No. 16/426,412, dated Jan. 6, 2020.
(Continued)

*Primary Examiner* — Rebecca E Eisenberg

(57) ABSTRACT

A method includes moving an actuation lock of a medical injector from a first position to a second position. The actuation lock has an extended portion disposed between a shoulder of a housing and the base when the actuation lock is in the first position. The extended portion is spaced apart from the base when the actuation lock is in the second position. A distal end portion of a base, which is movably coupled to an end portion of the housing, is placed into contact with a body. The base is actuated after the placing to release an energy from an energy storage member within the housing to produce a force to move a needle from a first needle position to a second needle position. At least a portion of the needle extends through the base when the needle is in the second needle position.

14 Claims, 34 Drawing Sheets

Related U.S. Application Data continuation of application No. 15/631,076, filed on Jun. 23, 2017, now Pat. No. 10,335,549, which is a continuation of application No. 14/731,048, filed on Jun. 4, 2015, now Pat. No. 9,737,669, which is a continuation of application No. 14/107,711, filed on Dec. 16, 2013, now Pat. No. 9,056,170, which is a continuation of application No. 13/053,451, filed on Mar. 22, 2011, now Pat. No. 8,608,698, which is a continuation of application No. 12/688,314, filed on Jan. 15, 2010, now Pat. No. 7,918,823, which is a continuation of application No. 11/758,393, filed on Jun. 5, 2007, now Pat. No. 7,648,483, which is a continuation-in-part of application No. 11/562,061, filed on Nov. 21, 2006, now Pat. No. 7,648,482, which is a continuation-in-part of application No. 10/572,148, filed as application No. PCT/US2006/003415 on Feb. 1, 2006, now Pat. No. 7,749,194, said application No. 11/562,061 is a continuation-in-part of application No. 10/515,571, filed as application No. PCT/US2004/039386 on Nov. 23, 2004, now Pat. No. 7,416,540.

(60) Provisional application No. 60/731,886, filed on Oct. 31, 2005, provisional application No. 60/648,822, filed on Feb. 1, 2005.

(51) Int. Cl.

| | | |
|---|---|---|
| *A61M 5/315* | (2006.01) | |
| *B65B 55/02* | (2006.01) | |
| *B65B 3/00* | (2006.01) | |
| *A61M 5/19* | (2006.01) | |
| *A61M 5/32* | (2006.01) | |
| *A61M 5/31* | (2006.01) | |
| *A61M 5/24* | (2006.01) | |

(52) U.S. Cl.
CPC ...... *A61M 5/31565* (2013.01); *A61M 5/3202* (2013.01); *A61M 5/3204* (2013.01); *A61M 5/326* (2013.01); *B65B 3/003* (2013.01); *B65B 55/02* (2013.01); *A61M 5/2053* (2013.01); *A61M 5/24* (2013.01); *A61M 5/2459* (2013.01); *A61M 5/3129* (2013.01); *A61M 5/31591* (2013.01); *A61M 2005/206* (2013.01); *A61M 2005/2013* (2013.01); *A61M 2005/2073* (2013.01); *A61M 2205/14* (2013.01); *A61M 2205/3576* (2013.01); *A61M 2205/50* (2013.01); *A61M 2205/502* (2013.01); *A61M 2205/581* (2013.01); *A61M 2205/582* (2013.01); *A61M 2205/583* (2013.01); *A61M 2205/6018* (2013.01); *A61M 2205/6036* (2013.01); *A61M 2207/00* (2013.01)

(56) References Cited

U.S. PATENT DOCUMENTS

| | | |
|---|---|---|
| 3,055,362 A | 9/1962 | Uytenbogaart |
| 3,115,133 A | 12/1963 | Morando |
| 3,426,448 A | 2/1969 | Sarnoff |
| 3,563,373 A | 2/1971 | Paulson |
| 3,565,070 A | 2/1971 | Hanson et al. |
| 3,688,765 A | 9/1972 | Gasaway |
| 3,768,472 A | 10/1973 | Hodosh et al. |
| 3,795,061 A | 3/1974 | Sarnoff et al. |
| 3,797,489 A | 3/1974 | Sarnoff |
| 3,941,130 A | 3/1976 | Tibbs |
| 3,945,379 A | 3/1976 | Pritz et al. |
| 4,031,889 A | 6/1977 | Pike |
| 4,086,062 A | 4/1978 | Hach |
| 4,108,177 A | 8/1978 | Pistor |
| 4,124,024 A | 11/1978 | Schwebel et al. |
| 4,226,235 A | 10/1980 | Sarnoff et al. |
| 4,227,528 A | 10/1980 | Wardlaw |
| 4,258,713 A | 3/1981 | Wardlaw |
| 4,360,019 A | 11/1982 | Portner et al. |
| 4,378,015 A | 3/1983 | Wardlaw |
| 4,394,863 A | 7/1983 | Bartner |
| 4,424,057 A | 1/1984 | House |
| 4,425,120 A | 1/1984 | Sampson et al. |
| 4,441,629 A | 4/1984 | Mackal |
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,664,653 A | 5/1987 | Sagstetter et al. |
| 4,666,430 A | 5/1987 | Brown et al. |
| 4,673,657 A | 6/1987 | Christian |
| 4,681,567 A | 7/1987 | Masters et al. |
| 4,689,042 A | 8/1987 | Sarnoff et al. |
| 4,693,708 A | 9/1987 | Wanderer et al. |
| 4,755,169 A | 7/1988 | Sarnoff et al. |
| 4,781,697 A | 11/1988 | Slaughter |
| 4,782,841 A | 11/1988 | Lopez |
| 4,784,652 A | 11/1988 | Wikström |
| 4,790,824 A | 12/1988 | Morrow et al. |
| 4,795,433 A | 1/1989 | Sarnoff |
| 4,822,340 A | 4/1989 | Kamstra |
| 4,826,489 A | 5/1989 | Haber |
| 4,853,521 A | 8/1989 | Claeys et al. |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,042,977 A | 8/1991 | Bechtold et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,842 A | 3/1992 | Bechtold et al. |
| 5,092,843 A | 3/1992 | Monroe et al. |
| 5,104,380 A | 4/1992 | Holman et al. |
| 5,125,898 A | 6/1992 | Kaufhold, Jr. et al. |
| 5,147,311 A | 9/1992 | Pickhard |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,244,465 A | 9/1993 | Michel |
| 5,271,527 A | 12/1993 | Haber et al. |
| 5,281,198 A | 1/1994 | Haber et al. |
| 5,286,258 A | 2/1994 | Haber et al. |
| 5,295,965 A | 3/1994 | Wilmot |
| 5,298,023 A | 3/1994 | Haber et al. |
| 5,312,326 A | 5/1994 | Myers et al. |
| 5,314,412 A | 5/1994 | Rex |
| 5,318,544 A | 6/1994 | Drypen et al. |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,358,489 A | 10/1994 | Wyrick |
| 5,363,842 A | 11/1994 | Mishelevich et al. |
| 5,380,281 A | 1/1995 | Tomellini et al. |
| 5,383,851 A | 1/1995 | McKinnon, Jr. et al. |

(56) References Cited

U.S. PATENT DOCUMENTS

| | | |
|---|---|---|
| 5,383,864 A | 1/1995 | van den Heuvel |
| 5,395,345 A | 3/1995 | Gross |
| 5,399,163 A | 3/1995 | Peterson et al. |
| 5,417,660 A | 5/1995 | Martin |
| 5,451,210 A | 9/1995 | Kramer et al. |
| 5,466,217 A | 11/1995 | Myers et al. |
| 5,478,316 A | 12/1995 | Bitdinger et al. |
| 5,514,097 A | 5/1996 | Knauer |
| 5,514,135 A | 5/1996 | Earle |
| 5,527,287 A | 6/1996 | Miskinyar |
| 5,540,664 A | 7/1996 | Wyrick |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,615,771 A | 4/1997 | Hollister |
| 5,616,132 A | 4/1997 | Newman |
| 5,645,534 A | 7/1997 | Chanoch |
| 5,658,259 A | 8/1997 | Pearson et al. |
| 5,681,291 A | 10/1997 | Galli |
| 5,681,292 A | 10/1997 | Tober et al. |
| 5,695,476 A | 12/1997 | Harris |
| 5,716,338 A | 2/1998 | Hjertman et al. |
| 5,728,074 A | 3/1998 | Castellano et al. |
| 5,734,109 A | 3/1998 | Thanscheidt |
| 5,772,635 A | 6/1998 | Dastur et al. |
| 5,779,677 A | 7/1998 | Frezza |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,570 A | 9/1998 | Fuchs et al. |
| 5,814,020 A | 9/1998 | Gross |
| 5,820,602 A | 10/1998 | Kovelman |
| 5,823,346 A | 10/1998 | Weiner |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,990 A | 12/1998 | Cirelli et al. |
| 5,852,590 A | 12/1998 | de la Huerga |
| 5,853,292 A | 12/1998 | Eggert et al. |
| 5,858,001 A | 1/1999 | Tsals et al. |
| 5,865,795 A | 2/1999 | Schiff et al. |
| 5,868,711 A | 2/1999 | Kramer et al. |
| 5,868,713 A | 2/1999 | Klippenstein |
| 5,868,721 A | 2/1999 | Marinacci |
| D407,487 S | 3/1999 | Greubel et al. |
| 5,876,380 A | 3/1999 | Manganini et al. |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |
| 5,971,953 A | 10/1999 | Bachynsky |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,050,977 A | 4/2000 | Adams |
| 6,056,728 A | 5/2000 | von Schuckmann |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,080,130 A | 6/2000 | Castellano |
| 6,083,199 A | 7/2000 | Thorley et al. |
| 6,084,526 A | 7/2000 | Blotky et al. |
| 6,086,562 A | 7/2000 | Jacobsen et al. |
| 6,096,002 A | 8/2000 | Landau |
| 6,099,503 A | 8/2000 | Stradella |
| 6,099,504 A | 8/2000 | Gross et al. |
| 6,102,896 A | 8/2000 | Roser |
| 6,119,684 A | 9/2000 | Nöhl et al. |
| 6,120,786 A | 9/2000 | Cheikh |
| 6,123,685 A | 9/2000 | Reynolds |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,179,812 B1 | 1/2001 | Botich et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,258,063 B1 | 7/2001 | Haar et al. |
| 6,258,068 B1 | 7/2001 | Kirchhofer et al. |
| 6,259,654 B1 | 7/2001 | de la Huerga |
| 6,264,629 B1 | 7/2001 | Landau |
| 6,270,479 B1 | 8/2001 | Bergens et al. |
| 6,280,421 B1 | 8/2001 | Kirchhofer et al. |
| 6,312,412 B1 | 11/2001 | Saied et al. |
| 6,317,630 B1 | 11/2001 | Gross et al. |
| 6,334,070 B1 | 12/2001 | Nova et al. |
| 6,364,866 B1 | 4/2002 | Furr et al. |
| 6,371,939 B2 | 4/2002 | Bergens et al. |
| 6,383,168 B1 | 5/2002 | Landau et al. |
| 6,387,078 B1 | 5/2002 | Gillespie, III |
| 6,405,912 B2 | 6/2002 | Giannou |
| 6,406,455 B1 | 6/2002 | Willis et al. |
| 6,411,567 B1 | 6/2002 | Niemiec et al. |
| 6,413,236 B1 | 7/2002 | Van Dyke |
| 6,425,897 B2 | 7/2002 | Overes et al. |
| 6,427,684 B2 | 8/2002 | Ritsche et al. |
| 6,428,517 B1 | 8/2002 | Hochman et al. |
| 6,428,528 B2 | 8/2002 | Sadowski |
| 6,475,181 B1 | 11/2002 | Potter et al. |
| 6,478,771 B1 | 11/2002 | Lavi et al. |
| 6,482,186 B1 | 11/2002 | Douglas et al. |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,597,794 B2 | 7/2003 | Cole et al. |
| 6,599,272 B1 | 7/2003 | Hjertman et al. |
| 6,613,010 B2 | 9/2003 | Castellano |
| 6,613,011 B2 | 9/2003 | Castellano |
| 6,616,627 B2 | 9/2003 | Willis et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,648,850 B2 | 11/2003 | Landau |
| 6,656,163 B1 | 12/2003 | Marshall et al. |
| 6,673,035 B1 | 1/2004 | Rice et al. |
| 6,676,630 B2 | 1/2004 | Landau et al. |
| 6,689,093 B2 | 2/2004 | Landau |
| 6,692,469 B1 | 2/2004 | Weekes et al. |
| 6,702,778 B2 | 3/2004 | Hill et al. |
| 6,706,019 B1 | 3/2004 | Parker et al. |
| 6,707,763 B2 | 3/2004 | Osberg et al. |
| 6,708,050 B2 | 3/2004 | Carim |

(56) References Cited

U.S. PATENT DOCUMENTS

| | | |
|---|---|---|
| 6,722,916 B2 | 4/2004 | Buccinna et al. |
| 6,723,077 B2 | 4/2004 | Pickup et al. |
| 6,726,657 B1 | 4/2004 | Dedig et al. |
| 6,726,661 B2 | 4/2004 | Munk et al. |
| 6,736,796 B2 | 5/2004 | Shekalim |
| 6,743,203 B1 | 6/2004 | Pickhard |
| 6,743,635 B2 | 6/2004 | Neel et al. |
| 6,749,437 B2 | 6/2004 | Chan |
| 6,752,781 B2 | 6/2004 | Landau et al. |
| 6,764,469 B2 | 7/2004 | Broselow |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,786,875 B2 | 9/2004 | Barker et al. |
| 6,793,646 B1 | 9/2004 | Giambattista et al. |
| 6,803,856 B1 | 10/2004 | Murphy et al. |
| 6,805,686 B1 | 10/2004 | Fathallah et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |
| 6,893,420 B2 | 5/2005 | Arnisolle |
| 6,923,764 B2 | 8/2005 | Aceti et al. |
| 6,936,029 B2 | 8/2005 | Mann et al. |
| 6,936,032 B1 | 8/2005 | Bush, Jr. et al. |
| 6,937,150 B2 | 8/2005 | Medema et al. |
| 6,942,646 B2 | 9/2005 | Langley et al. |
| 6,946,299 B2 | 9/2005 | Neel et al. |
| 6,948,492 B2 | 9/2005 | Wermeling et al. |
| 6,949,082 B2 | 9/2005 | Langley et al. |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,074,211 B1 | 7/2006 | Heiniger et al. |
| 7,104,972 B2 | 9/2006 | Moller et al. |
| 7,113,101 B2 | 9/2006 | Peterson et al. |
| 7,116,233 B2 | 10/2006 | Zhurin |
| 7,118,553 B2 | 10/2006 | Scherer |
| 7,126,879 B2 | 10/2006 | Snyder |
| 7,158,011 B2 | 1/2007 | Brue |
| 7,241,278 B2 | 7/2007 | Moller |
| 7,329,241 B2 | 2/2008 | Horvath et al. |
| 7,357,790 B2 | 4/2008 | Hommann et al. |
| 7,416,540 B2 | 8/2008 | Edwards et al. |
| 7,465,294 B1 | 12/2008 | Vladimirsky |
| 7,500,963 B2 | 3/2009 | Westbye et al. |
| 7,500,967 B2 | 3/2009 | Thorley et al. |
| 7,503,907 B1 | 3/2009 | Lesch, Jr. |
| 7,544,188 B2 | 6/2009 | Edwards et al. |
| 7,611,491 B2 | 11/2009 | Pickhard |
| 7,611,495 B1 | 11/2009 | Gianturco |
| 7,618,396 B2 | 11/2009 | Slate et al. |
| 7,637,891 B2 | 12/2009 | Wall |
| 7,648,482 B2 | 1/2010 | Edwards et al. |
| 7,648,483 B2 | 1/2010 | Edwards et al. |
| 7,674,246 B2 | 3/2010 | Gillespie et al. |
| 7,686,788 B2 | 3/2010 | Freyman et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,758,550 B2 | 7/2010 | Bollenbach et al. |
| 7,771,397 B1 | 8/2010 | Olson |
| 7,806,866 B2 | 10/2010 | Hommann et al. |
| 7,850,662 B2 | 12/2010 | Veasey et al. |
| 7,901,377 B1 | 3/2011 | Harrison et al. |
| 7,901,384 B2 | 3/2011 | Kleyman et al. |
| 7,918,823 B2 | 4/2011 | Edwards et al. |
| 7,918,832 B2 | 4/2011 | Veasey et al. |
| 7,938,802 B2 | 5/2011 | Bicknell et al. |
| 7,938,808 B2 | 5/2011 | Pessin |
| 7,947,017 B2 | 5/2011 | Edwards et al. |
| 8,016,788 B2 | 9/2011 | Edwards et al. |
| 8,021,335 B2 | 9/2011 | Lesch, Jr. |
| 8,105,281 B2 | 1/2012 | Edwards et al. |
| 8,105,293 B2 | 1/2012 | Pickhard |
| 8,123,719 B2 | 2/2012 | Edwards et al. |
| 8,162,886 B2 | 4/2012 | Sadowski et al. |
| 8,172,082 B2 | 5/2012 | Edwards et al. |
| 8,172,790 B2 | 5/2012 | Hunter et al. |
| 8,221,347 B2 | 7/2012 | Toles et al. |
| 8,251,947 B2 | 8/2012 | Kramer et al. |
| 8,276,583 B2 | 10/2012 | Farieta et al. |
| 8,313,466 B2 | 11/2012 | Edwards et al. |
| 8,343,130 B2 | 1/2013 | Green |
| 8,361,029 B2 | 1/2013 | Edwards et al. |
| 8,425,462 B2 | 4/2013 | Edwards et al. |
| 8,608,698 B2 | 12/2013 | Edwards et al. |
| 8,613,720 B2 | 12/2013 | Bendek et al. |
| 8,684,968 B2 | 4/2014 | Genosar |
| 8,728,042 B2 | 5/2014 | Pickhard |
| 8,734,392 B2 | 5/2014 | Stadelhofer |
| 8,747,357 B2 | 6/2014 | Stamp et al. |
| 8,920,367 B2 | 12/2014 | Edwards et al. |
| 8,920,377 B2 | 12/2014 | Edwards et al. |
| 8,939,959 B2 | 1/2015 | Baney et al. |
| 9,022,980 B2 | 5/2015 | Edwards et al. |
| 9,056,170 B2 | 6/2015 | Edwards et al. |
| 9,084,849 B2 | 7/2015 | Edwards et al. |
| 9,149,579 B2 | 10/2015 | Edwards et al. |
| 9,173,999 B2 | 11/2015 | Edwards et al. |
| 10,071,203 B2 | 9/2018 | Edwards et al. |
| 11,167,087 B2 | 11/2021 | Meyers et al. |
| 2001/0005781 A1 | 6/2001 | Bergens et al. |
| 2001/0037087 A1 | 11/2001 | Knauer |
| 2002/0055711 A1 | 5/2002 | Lavi et al. |
| 2002/0076679 A1 | 6/2002 | Aman |
| 2002/0079326 A1 | 6/2002 | Fuchs |
| 2002/0095120 A1 | 7/2002 | Larsen et al. |
| 2002/0189612 A1 | 12/2002 | Rand |
| 2003/0028145 A1 | 2/2003 | Duchon et al. |
| 2003/0040717 A1 | 2/2003 | Saulenas et al. |
| 2003/0105430 A1 | 6/2003 | Lavi et al. |
| 2003/0106824 A1 | 6/2003 | Wilmot et al. |
| 2003/0120222 A1 | 6/2003 | Vaillancourt |
| 2003/0132128 A1 | 7/2003 | Mazur |
| 2003/0233070 A1 | 12/2003 | De La Serna et al. |
| 2004/0019326 A1 | 1/2004 | Gilbert et al. |
| 2004/0024361 A1 | 2/2004 | Fago et al. |
| 2004/0024367 A1 | 2/2004 | Gilbert |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0054327 A1 | 3/2004 | Gillespie, III |
| 2004/0073169 A1 | 4/2004 | Amisar et al. |
| 2004/0092874 A1 | 5/2004 | Mazidji |
| 2004/0092875 A1 | 5/2004 | Kochamba |
| 2004/0094146 A1 | 5/2004 | Schiewe et al. |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0220524 A1 | 11/2004 | Sadowski et al. |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0049561 A1 | 3/2005 | Hommann et al. |
| 2005/0062603 A1 | 3/2005 | Fuerst et al. |

(56) References Cited

U.S. PATENT DOCUMENTS

| | | |
|---|---|---|
| 2005/0070848 A1 | 3/2005 | Kim |
| 2005/0090781 A1 | 4/2005 | Baba et al. |
| 2005/0090782 A1 | 4/2005 | Marshall et al. |
| 2005/0101912 A1 | 5/2005 | Faust et al. |
| 2005/0134433 A1 | 6/2005 | Sweeney, II |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |
| 2005/0171477 A1 | 8/2005 | Rubin et al. |
| 2005/0182358 A1 | 8/2005 | Veit et al. |
| 2005/0183982 A1 | 8/2005 | Giewercer |
| 2005/0192534 A1 | 9/2005 | Wolbring et al. |
| 2005/0197654 A1 | 9/2005 | Edman et al. |
| 2005/0203466 A1 | 9/2005 | Hommann et al. |
| 2005/0222539 A1 | 10/2005 | Gonzales et al. |
| 2005/0261742 A1 | 11/2005 | Nova et al. |
| 2005/0267403 A1 | 12/2005 | Landau et al. |
| 2005/0273059 A1 | 12/2005 | Mernoe et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0069350 A1 | 3/2006 | Buenger et al. |
| 2006/0074519 A1 | 4/2006 | Barker et al. |
| 2006/0111666 A1 | 5/2006 | Hommann et al. |
| 2006/0111671 A1 | 5/2006 | Klippenstein |
| 2006/0129089 A1 | 6/2006 | Stamp |
| 2006/0129090 A1 | 6/2006 | Moberg et al. |
| 2006/0173408 A1 | 8/2006 | Wyrick |
| 2006/0184133 A1 | 8/2006 | Pessin |
| 2006/0189938 A1 | 8/2006 | Hommann et al. |
| 2006/0200077 A1 | 9/2006 | Righi et al. |
| 2006/0204939 A1 | 9/2006 | Bardsley et al. |
| 2006/0223027 A1 | 10/2006 | Smith et al. |
| 2006/0235354 A1 | 10/2006 | Kaal et al. |
| 2006/0247578 A1 | 11/2006 | Arguendas et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0074722 A1 | 4/2007 | Giroux et al. |
| 2007/0079777 A1 | 4/2007 | Hurlstone et al. |
| 2007/1002881 | 5/2007 | Bozeman et al. |
| 2007/0129686 A1 | 6/2007 | Daily et al. |
| 2007/0135767 A1 | 6/2007 | Gillespie, III et al. |
| 2007/0173772 A1 | 7/2007 | Liversidge |
| 2007/0184847 A1 | 8/2007 | Hansen et al. |
| 2007/0210147 A1 | 9/2007 | Morrone et al. |
| 2007/0213598 A1 | 9/2007 | Howard et al. |
| 2007/0265568 A1 | 11/2007 | Tsals et al. |
| 2007/0276320 A1 | 11/2007 | Wall et al. |
| 2007/0293826 A1 | 12/2007 | Wall et al. |
| 2008/0147006 A1 | 6/2008 | Brunnberg et al. |
| 2008/0154200 A1 | 6/2008 | Lesch |
| 2008/0171995 A1 | 7/2008 | Vitullo et al. |
| 2008/0188798 A1 | 8/2008 | Weber |
| 2008/0228143 A1 | 9/2008 | Stamp |
| 2008/0255513 A1 | 10/2008 | Kaal et al. |
| 2008/0262443 A1 | 10/2008 | Hommann et al. |
| 2009/0005735 A1 | 1/2009 | Wikner et al. |
| 2009/0093759 A1 | 4/2009 | Judd et al. |
| 2009/0192486 A1 | 7/2009 | Wilmot et al. |
| 2009/0221962 A1 | 9/2009 | Kaal et al. |
| 2009/0240200 A1 | 9/2009 | Heneveld et al. |
| 2009/0318361 A1 | 12/2009 | Noera et al. |
| 2010/0010454 A1 | 1/2010 | Marshall et al. |
| 2010/0049125 A1 | 2/2010 | James et al. |
| 2010/0152659 A1 | 6/2010 | Streit et al. |
| 2010/0160894 A1 | 6/2010 | Julian et al. |
| 2010/0185148 A1 | 7/2010 | Gillespie, III et al. |
| 2010/0212663 A1 | 8/2010 | Vedrine et al. |
| 2011/0060274 A1 | 3/2011 | Kuhn |
| 2011/0077589 A1 | 3/2011 | Karlsson et al. |
| 2011/0201999 A1 | 8/2011 | Cronenberg |
| 2011/0245761 A1 | 10/2011 | Jennings et al. |
| 2011/0295215 A1 | 12/2011 | Nielsen et al. |
| 2012/0107783 A1 | 5/2012 | Julian et al. |
| 2012/0289929 A1 | 11/2012 | Boyd et al. |
| 2013/0079718 A1 | 3/2013 | Shang et al. |
| 2013/0317477 A1 | 11/2013 | Edwards et al. |
| 2015/0238695 A1 | 8/2015 | Edwards et al. |
| 2016/0015907 A1 | 1/2016 | Edwards et al. |
| 2016/0184521 A1 | 6/2016 | Edwards et al. |
| 2016/0250414 A1 | 9/2016 | Edwards et al. |
| 2017/0290982 A1 | 10/2017 | Edwards et al. |
| 2018/0008774 A1 | 1/2018 | Edwards et al. |
| 2018/0304017 A1 | 10/2018 | Edwards et al. |
| 2018/0304018 A1 | 10/2018 | Blondino et al. |
| 2019/0009027 A1 | 1/2019 | Edwards et al. |
| 2019/0175837 A1 | 6/2019 | Edwards et al. |
| 2019/0275253 A1 | 9/2019 | Edwards et al. |
| 2019/0282763 A1 | 9/2019 | Edwards et al. |
| 2019/0328971 A1 | 10/2019 | Edwards et al. |
| 2019/0358399 A1 | 11/2019 | Edwards et al. |
| 2020/0197612 A1 | 6/2020 | Edwards et al. |
| 2021/0138152 A1 | 5/2021 | Edwards et al. |
| 2022/0040413 A1 | 2/2022 | Edwards et al. |
| 2022/0054753 A1 | 2/2022 | Meyers et al. |

FOREIGN PATENT DOCUMENTS

| | | |
|---|---|---|
| EP | 1712178 A2 | 10/2006 |
| FR | 1514210 | 2/1968 |
| FR | 2506161 | 11/1982 |
| FR | 2509615 | 1/1983 |
| FR | 2700959 | 2/1993 |
| WO | WO 91/04760 | 4/1991 |
| WO | WO 93/02720 | 2/1993 |
| WO | WO 95/13838 | 5/1995 |
| WO | WO 95/26009 | 9/1995 |
| WO | WO 95/35126 | 12/1995 |
| WO | WO 98/52632 | 11/1998 |
| WO | WO 99/10031 | 3/1999 |
| WO | WO 2001/024690 | 4/2001 |
| WO | WO 2001/026020 | 4/2001 |
| WO | WO 2001/088828 | 11/2001 |
| WO | WO 2001/093926 | 12/2001 |
| WO | WO 2002/083205 | 10/2002 |
| WO | WO 2002/083212 | 10/2002 |
| WO | WO 2002/100469 | 12/2002 |
| WO | WO 2003/011378 | 2/2003 |
| WO | WO 2003/013632 | 2/2003 |
| WO | WO 2003/095001 | 11/2003 |
| WO | WO 2003/097133 | 11/2003 |
| WO | WO 2004/047890 | 6/2004 |
| WO | WO 2004/047891 | 6/2004 |
| WO | WO 2004/047892 | 6/2004 |
| WO | WO 2004/047893 | 6/2004 |
| WO | WO 2004/054644 | 7/2004 |
| WO | WO 2005/050526 | 6/2005 |
| WO | WO 2005/070481 | 8/2005 |
| WO | WO 2005/077441 | 8/2005 |
| WO | WO 2005/039673 | 5/2006 |
| WO | WO 2006/109778 | 10/2006 |
| WO | WO 2006/125692 | 11/2006 |
| WO | WO 2007/083115 | 7/2007 |
| WO | WO 2008/005315 | 1/2008 |
| WO | WO 2008/148864 | 12/2008 |
| WO | WO 2010/033806 | 3/2010 |
| WO | WO 2013/044172 | 3/2013 |

OTHER PUBLICATIONS

Office Action for IN Application No. 201718041270, dated May 24, 2021.

Office Action for U.S. Appl. No. 16/246,412, dated Sep. 17, 2019.

"Solutions for Medical Devices," 3M Brochure, © 3M, (2006), 80-6201-3490-0, 8 pages.

Tingelstad, M., "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=articlePrint&ArticleID=CA6332947>, 3 pages.

(56) References Cited

OTHER PUBLICATIONS

"Flexible circuits / Flex circuits / Flexible Technology Ltd.," Flexible Technology Limited [online] [retrieved on Aug. 28, 2006] Retrieved from the Internet <URL: http://www.flexibletechnology.com/ >, 2 pages.
"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible circuitsCapability.htm >, 2 pages.
"Flex Circuits/flexible circuits design guide," [online] [retrieved on Aug. 28, 2006] Retrieved from the Internet <URL: http://flexiblecircuit.co.uk/Flex Circuits Design Guide.htm >, 7 pages.
"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >, 3 pages.
"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/product catalogue.asp >, 9 pages.
"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >, 3 pages.
Allan, R., "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1 &ArticleID=2041 >, 3 pages.
RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >, 2 pages.
"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8>, 3 pages.
Scholz, O., "Drug depot in a tooth," [online] [retrieved on Feb. 6, 2007] Retrieved from the Internet <URL: http://www.fraunhofer.de/fhg/EN/press/pi/2007/02Mediendienst22007Thema2.jsp?print=true>, 1 page.
Heartsine Technology, samaritan™ PAD Accessories [online] [retrieved on Jun. 1, 2007] Retrieved from the Internet <URL: http://www.heartsine.com/aboutsam-accessories.htm>, 4 pages.
CliniSense Corporation, "Drug delivery devices A potentially harsh environment for drugs," Stability [online] [retrieved on Jun. 1, 2007] Retrieved from the Internet <URL: http://www.clinisense.com/devices.htm>, 2 pages.
CliniSense Corporation, "LifeTrack Technology A new method to detect improper storage." Stability [online] [retrieved on Jun. 1, 2007] Retrieved from the Internet <URL: http://www.clinisense.com/tech.htm>, 2 pages.
AED Professionals™ Brochure [online] [retrieved on Jun. 1, 2007] Retrieved from the Internet <URL: http://www.aedprofessionals.com>, 4 pages.
Ruppar, D., "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-oniine.com/drugdelivery/200702/templates/pageviewer_print?pg=44&pm=8 >, 8 pages.
Office Action for Canadian Patent Application No. 2,586,525, dated Aug. 17, 2010.
Examination Report for British Patent Application No. GB 0708523.6, dated Dec. 8, 2008.
Examination Report for British Patent Application No. GB 0822532.8, dated Jan. 21, 2009.
Examination Report for British Patent Application No. GB 0822532.8, dated May 21, 2009.
Office Action for U.S. Appl. No. 11/562,061, dated Feb. 3, 2009.
Office Action for U.S. Appl. No. 11/566,422, dated Jul. 6, 2010.
Office Action for U.S. Appl. No. 11/566,422, dated Dec. 3, 2010.
Office Action for Japanese Patent Application No. 2009-537380, dated Jun. 15, 2012.
Office Action for U.S. Appl. No. 11/758,393, dated May 13, 2009.
Search Report and Written Opinion for International Patent Application No. PCT/US07/84891 dated Sep. 15, 2008, 7 pages.
Office Action for U.S. Appl. No. 12/138,987, dated Oct. 5, 2009.
Office Action for U.S. Appl. No. 13/090,392, dated Feb. 29, 2012.
International Search Report and Written Opinion for International Patent Application No. PCT/US06/03415, dated Jul. 13, 2006, 10 pages.
International Search Report and Written Opinion for International Patent Application No. PCT/US07/007626, dated Sep. 29, 2008.
Office Action for Canadian Patent Application No. 2,762,072, dated Mar. 14, 2016.
Third Party Observations filed in European Patent Application No. 07864490.3, dated Aug. 22, 2016.
Office Action for U.S. Appl. No. 14/731,048, dated Oct. 19, 2016.
Office Action for India Patent Application No. 3988/DELP/2009, dated Mar. 31, 2017.
Office Action for U.S. Appl. No. 15/631,076, dated Apr. 8, 2019.

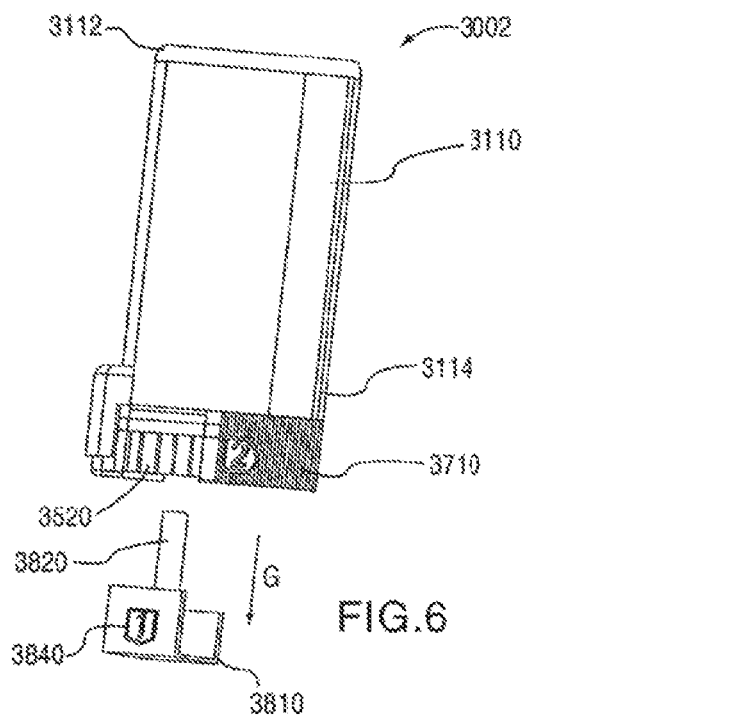
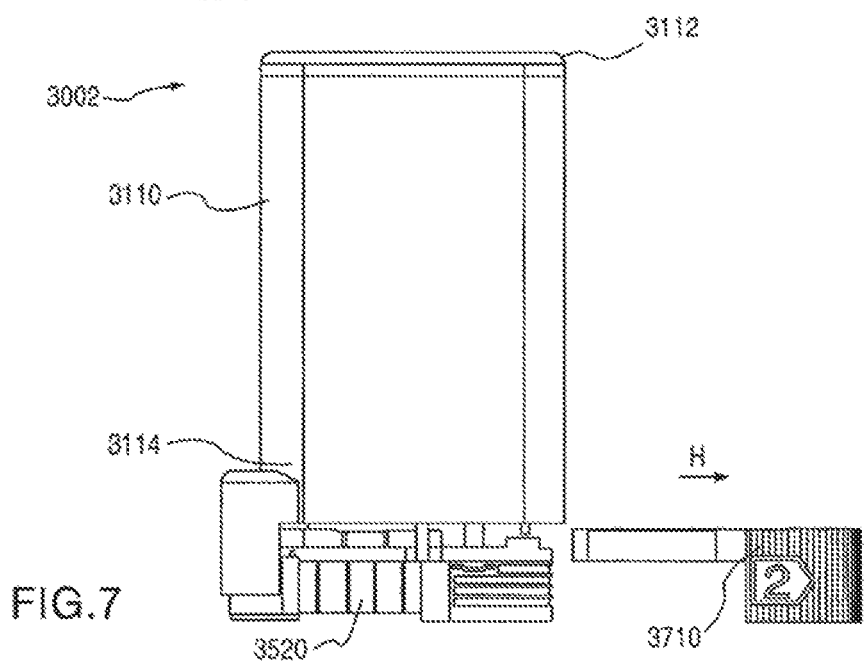

DEVICES, SYSTEMS AND METHODS FOR MEDICAMENT DELIVERY

CROSS-REFERENCE TO RELATED APPLICATIONS

This application is a divisional of U.S. patent application Ser. No. 16/426,412 entitled "Devices, Systems and Methods for Medicament Delivery," filed May 30, 2019, which is a continuation of U.S. patent application Ser. No. 15/631,076 entitled "Devices, Systems and Methods for Medicament Delivery," filed Jun. 23, 2017, which is a continuation of U.S. patent application Ser. No. 14/731,048, now U.S. Pat. No. 9,737,669, entitled "Devices, Systems and Methods for Medicament Delivery," filed Jun. 4, 2015, which is a continuation of U.S. patent Ser. No. 14/107,711, now U.S. Pat. No. 9,056,170, entitled "Devices, Systems and Methods for Medicament Delivery," filed Dec. 16, 2013, which is a continuation of U.S. patent application Ser. No. 13/053,451, now U.S. Pat. No. 8,608,698, entitled "Devices, Systems and Methods for Medicament Delivery," filed Mar. 22, 2011, which is a continuation of U.S. patent application Ser. No. 12/688,314, now U.S. Pat. No. 7,918,823, entitled "Devices, Systems and Methods for Medicament Delivery," filed Jan. 15, 2010, which is a continuation of U.S. patent application Ser. No. 11/758,393, now U.S. Pat. No. 7,648,483, entitled "Devices, Systems and Methods for Medicament Delivery," filed Jun. 5, 2007, which is a continuation-in-part of U.S. patent application Ser. No. 11/562,061, now U.S. Pat. No. 7,648,482, entitled "Devices, Systems and Methods for Medicament Delivery," filed Nov. 21, 2006, which is a continuation-in-part of U.S. patent application Ser. No. 10/515,571, now U.S. Pat. No. 7,416,540, entitled "Devices, Systems and Methods for Medicament Delivery," filed Nov. 23, 2004, which is a national stage filing under 35 U.S.C. § 371 of International Patent Application No. PCT/US2004/039386, entitled "Devices, Systems and Methods for Medicament Delivery," filed Nov. 23, 2004, each of which is incorporated herein by reference in its entirety. Said U.S. patent application Ser. No. 11/562,061 is a continuation-in-part of U.S. patent application Ser. No. 10/572,148, now U.S. Pat. No. 7,749,194, entitled "Devices, Systems and Methods for Medicament Delivery," filed Mar. 16, 2006, which is a national stage filing under 35 U.S.C. § 371 of International Patent Application No. PCT/US2006/003415, entitled "Devices, Systems and Methods for Medicament Delivery," filed Feb. 1, 2006, which claims priority to U.S. Provisional Application Ser. No. 60/648,822, entitled "Devices, Systems and Methods for Medicament Delivery," filed Feb. 1, 2005 and U.S. Provisional Application Ser. No. 60/731,886, entitled "Auto-Injector with Feedback," filed Oct. 31, 2005, each of which is incorporated herein by reference in its entirety.

BACKGROUND

The invention relates generally to a medical device, and more particularly to a medicament delivery device for automatically injecting a medicament into a body of a patient.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure.

Because emergency medical facilities may not be available when an individual is suffering from an allergic reaction, some individuals carry an auto-injector to rapidly self-administer a medicament in response to an allergic reaction.

Some known auto-injectors include a locking cap at the proximal end of the auto-injector to prevent inadvertent actuation and a needle cover at the distal end of the auto-injector. Such a configuration can, at times, cause a user to become confused as to which end of the auto-injector is the "needle end" (i.e., the distal end) and which end of the auto-injector is the "actuation end" (i.e., the proximal end). As such, in some situations, a user may mistakenly actuate the known auto-injector away from the intended injection site. Such an error can result, for example, in the auto-injector being actuated into the user's thumb and/or finger. Furthermore, the locking cap can be removed prior to removal of the needle cover, thus allowing the auto-injector to be actuated before the needle cover has been removed.

Some known auto-injectors include a needle cover that collapses or buckles when the auto-injector is actuated and the needle breaks through the cover. In application, this leaves the needle cover bunched around a portion of the needle, which can cause the needle cover to interfere with penetration of the needle into the user.

Manufacturing techniques of known auto-injectors require much of the manufacturing process of an auto-injector to occur in a sterile environment. In particular, a sterile environment is needed for filling the auto-injector with a medicament and for assembly of the auto-injector. Providing and maintaining a sterile environment during the entire manufacturing process, however, can be quite expensive.

Thus, a need exists for an auto-injector that can be more conveniently carried by a user and that can be actuated from its distal end. A need exists for an auto-injector that cannot be actuated until the needle cover has been removed. A need also exists for an auto-injector with a needle cover that will not interfere with, but will ensure, consistent penetration of the needle. Furthermore, a need exists for a more economical method of manufacturing auto-injectors.

SUMMARY

Apparatuses for automatic medicament injection and methods for manufacturing automatic medicament injectors are described herein. In some embodiments, an apparatus includes a housing, a needle, an energy storage member, an actuator, a locking member, and a needle guard. The needle is configured to move between a first position and a second position. In its first position, the needle is contained within the housing. In its second position, at least a portion of the needle extends from the housing. The energy storage member has a first configuration and a second configuration and is configured to produce a force when moving between its first configuration and its second configuration to move the needle from its first position to its second position. The actuator is configured to move the energy storage member from its first configuration to its second configuration. The locking member is movably coupled to the distal end portion of the housing such that the locking member can be moved between a first position and a second position. In its first position, the locking member is configured to engage the actuator to prevent the actuator from moving the energy storage member to the second configuration. The needle guard is removably coupled to at least one of the distal end portion of the housing or a base movably coupled to the distal end portion of the housing.

BRIEF DESCRIPTION OF THE DRAWINGS

FIG. 6 is a perspective view of the auto-injector illustrated in FIG. 3 showing an assembly according to an embodiment of the invention being removed.

FIG. 7 is a front view of the auto-injector illustrated in FIG. 3 showing a member according to an embodiment of the invention being removed.

DETAILED DESCRIPTION

Figure 1:
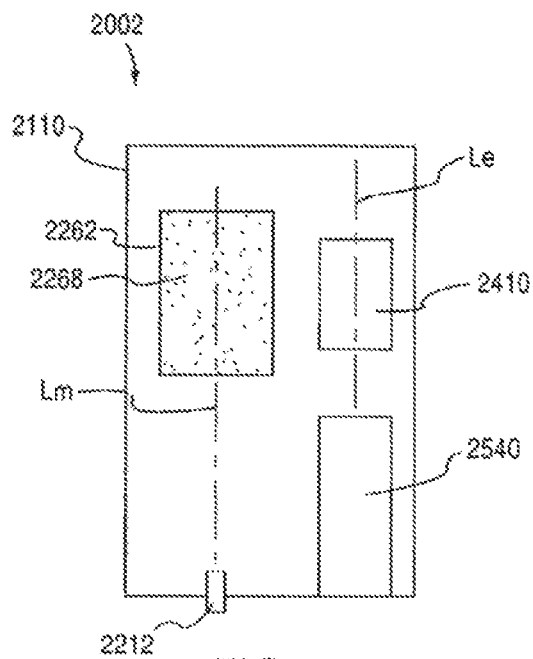
FIGS. 1 and 2 are schematic illustrations of an auto-injector according to an embodiment of the invention in a first configuration and a second configuration, respectively.

Apparatuses and methods for automatic medicament injection and methods for manufacturing automatic medicament injectors (also referred to herein as "auto-injectors") are described herein. In some embodiments, an apparatus includes a housing, a needle, an energy storage member, an actuator, a locking member, and a needle guard. The needle is configured to move between a first position and a second position. In its first position, the needle is contained within the housing. In its second position, at least a portion of the needle extends from the housing. The energy storage member has a first configuration and a second configuration and is configured to produce a force when moving between its first configuration and its second configuration to move the needle from its first position to its second position. The actuator is configured to move the energy storage member from its first configuration to its second configuration. The locking member is movably coupled to the distal end portion of the housing such that the locking member can be moved between a first position and a second position. In its first position, the locking member is configured to engage the actuator to prevent the actuator from moving the energy storage member to the second configuration. The needle guard is removably coupled to at least one of the distal end portion of the housing or a base movably coupled to the distal end portion of the housing.

In some embodiments, an apparatus includes a housing and a safety guard. The safety guard includes a locking portion and a needle guard portion. The locking portion is configured to inhibit actuation of a medicament delivery device. The needle guard portion is configured to substantially cover a needle of the medicament delivery device. The safety guard has a first position and a second position. In its first position, the safety guard is configured to be selectively coupled to at least one of the housing or a base movably coupled to the housing. In its second position, the safety guard is removed from the housing.

In some embodiments, an apparatus includes a needle guard configured to cover at least a portion of a needle of a medical injector. The needle guard is configured to substantially prevent microbes from passing through the needle guard. The needle guard is configured to allow a sterilant gas to pass through the needle guard.

In some embodiments, an apparatus includes a housing, a medicament injector, and a porous needle guard. The medicament injector is disposable within the housing and includes a needle. The needle has a first position and a second position. In its first position, the needle is contained within the housing. In its second position, at least a portion of the needle extends from the housing. The porous needle guard is removably coupled to the distal end portion of the housing. The porous needle guard is constructed from a microbial resistant material.

A method of manufacturing an automatic medicament injector includes inserting at least a portion of a needle into a needle hub disposed in a housing. A needle cover is installed over at least a portion of the needle to substantially cover a portion of the needle extending from the needle hub. The needle is sterilized after the needle cover is installed over at least a portion of the needle.

Figure 2:
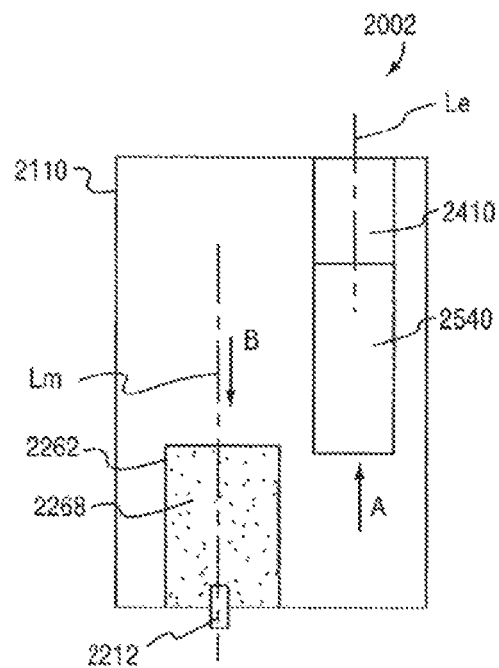

FIGS. 1 and 2 are schematic illustrations of an auto-injector 2002 according to an embodiment of the invention in a first configuration and a second configuration, respectively. The auto-injector 2002 includes a housing 2110 that contains a medicament container 2262, an energy storage member 2410, a release member 2540 and an injection member 2212. The medicament container 2262, which can be, for example, a pre-filled cartridge, a vial, an ampule or the like, is movably disposed within the housing 2110. The medicament container 2262 contains a medicament 2268, such as, for example, epinephrine. As illustrated, the medicament container 2262 can be moved, as indicated by arrow B in FIG. 2, along its longitudinal axis Lm between a first position (FIG. 1) and a second position (FIG. 2). When the medicament container 2262 is in its first (or retracted) position, the medicament container 2262 is spaced apart from the injection member 2212. When the medicament container 2262 is in the second (or advanced) position, the medicament container 2262 is placed in fluid communication with the injection member 2212. In this manner, when the medicament container 2262 is in the second (or advanced) position, the medicament 2268 can be conveyed via the injection member 2212 from the medicament container 2262 into a body of a patient. The injection member 2212 can be, for example, a needle, a nozzle or the like.

The energy storage member 2410, which can be any suitable device for storing energy, such as, for example, a spring, a battery, a compressed gas cylinder or the like, is also movably disposed within the housing 2110. As shown, the energy storage member 2410 defines a longitudinal axis Le that is offset from the longitudinal axis Lm of the medicament container 2262. The energy storage member 2410 can be moved, as indicated by arrow A in FIG. 2, within the housing 2110 along its longitudinal axis Le between a first position (FIG. 1) and a second position (FIG. 2). When the energy storage member 2410 is in its first position, the energy storage member 2410 has a first potential energy. When the energy storage member 2410 is in its second position, the energy storage member 2410 has a second potential energy that is less than the first potential energy. When the energy storage member 2410 moves from its first position to its second position, it converts at least a portion of its first potential energy into kinetic energy to move the medicament container 2262 between its first position and its second position.

Said another way, the movement of the energy storage member 2410 from its first position to its second position results in the production of a force that acts upon the medicament container 2262 to move the medicament container 2262 between its first position and its second position. The non-coaxial relationship between the longitudinal axis Lm of the medicament container 2262 and the longitudinal axis Le of the energy storage member 2410 allows the medicament container 2262 and the energy storage member 2410 to be arranged within the housing 2110 in any number of different configurations. In this manner, the auto-injector 2002 can have any number of different sizes and shapes, such as, for example, a substantially rectangular shape.

The release member 2540 is disposed within the housing 2110 and is configured to selectively deploy the energy storage member 2410 from its first position to its second position. The release member 2540 can be any suitable mechanism for moving the energy storage member 2410, such as, for example, a mechanical linkage, a spring-loaded rod or the like. In this manner, a user can actuate the auto-injector by manipulating a portion of the release member 2540.

Figure 3:
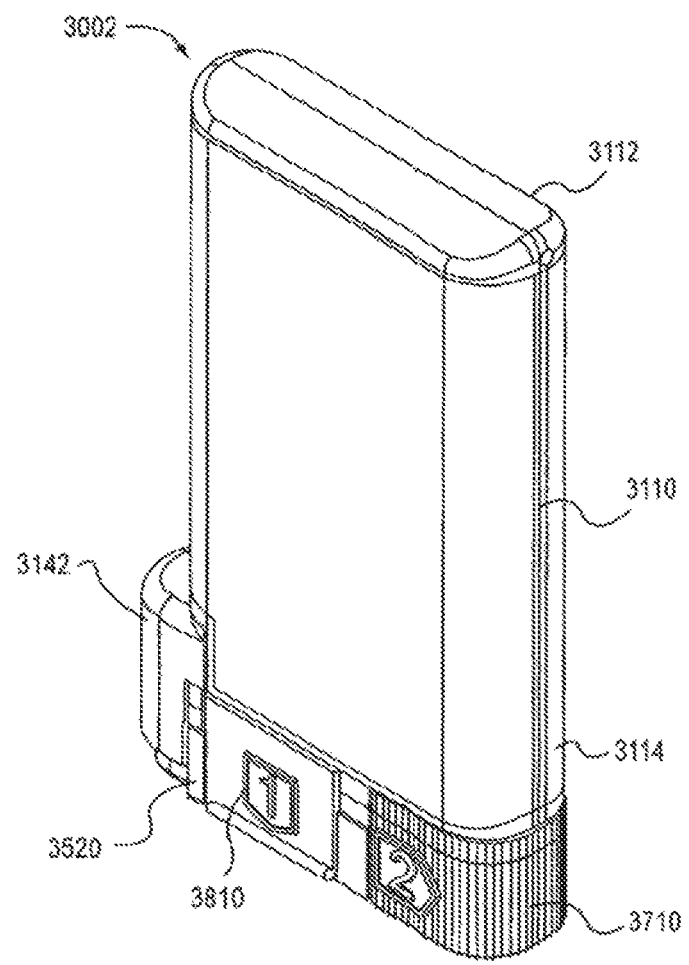
FIG. 3 is a perspective view of an auto-injector according to an embodiment of the invention.

FIG. 3 is a perspective view of an auto-injector 3002 according to an embodiment of the invention in a first configuration. The auto-injector 3002 includes a housing 3110 having a proximal end portion 3112 and a distal end portion 3114. The distal end portion 3114 of the housing 3110 includes a protrusion 3142 to help a user grasp and retain the housing 3110 when using the auto-injector 3002. Said another way, the protrusion 3142 is configured to prevent the auto-injector 3002 from slipping from the user's grasp during use. A base 3520 is movably coupled to the distal end portion 3114 of the housing 3110. A needle guard assembly 3810 is removably coupled to the base 3520. Similarly, a safety lock 3710 is removably coupled to the base 3520. To inject a medicament into the body, the distal end portion 3114 of the housing 3110 is oriented towards the user such that the base 3520 is in contact with the portion of the body where the injection is to be made. The base 3520 is then moved towards the proximal end 3112 of the housing 3110 to actuate the auto-injector 3002. The housing 3110 also includes a transparent status window 3118 (see FIG. 22) to allow a user to determine the status of the auto-injector 3002 or the medicament contained therein.

Figure 4:
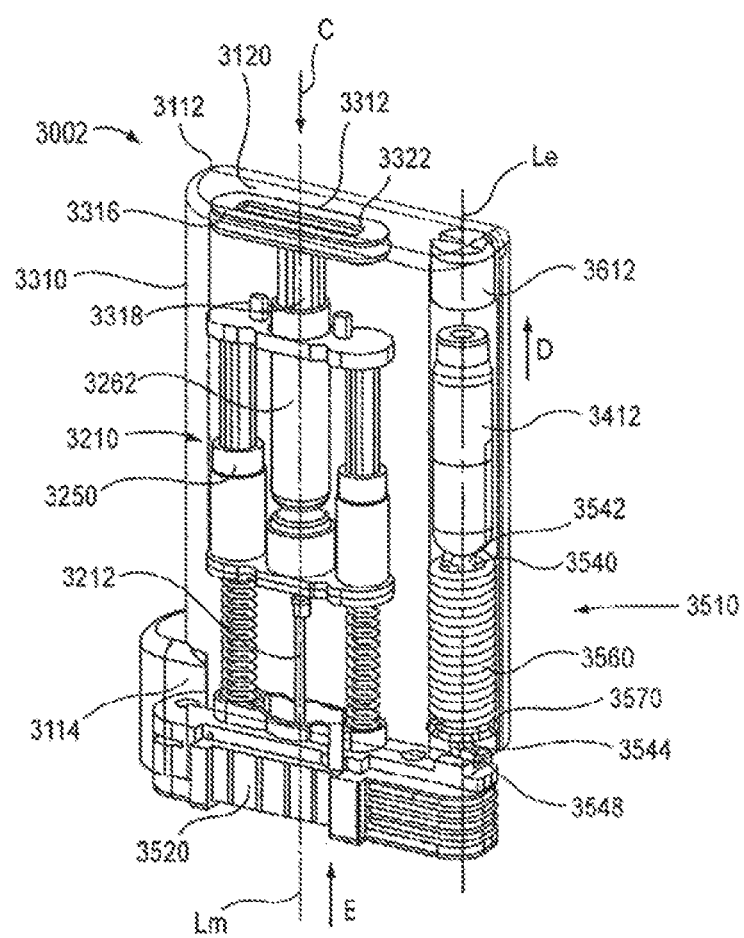
FIG. 4 is a perspective view of the auto-injector illustrated in FIG. 3 in a first configuration, with at least a portion of the auto-injector illustrated in phantom lines for ease of reference.
Figure 5:
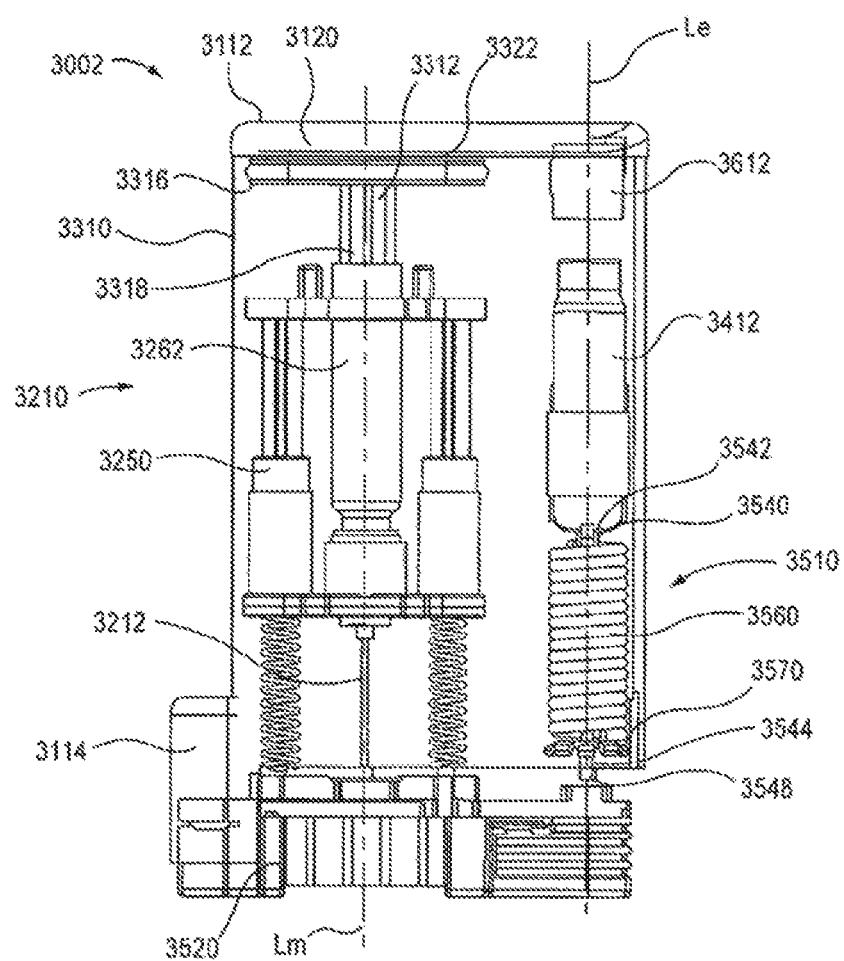
FIG. 5 is a front view of the auto-injector illustrated in FIGS. 3 and 4 in a first configuration.

FIG. 4 is a perspective view of the auto-injector 3002 showing the housing 3110 in phantom lines so that the components contained within the housing 3110 can be more clearly seen. For clarity, FIG. 4 shows the auto-injector 3002 without the needle guard assembly 3810 and the safety lock 3710. Similarly, FIG. 5 is a front view of the auto-injector 3002 showing the housing 3110 in phantom lines. The auto-injector 3002 includes a medicament injector 3210 and a movable member 3312 engaged with the medicament injector 3210, each of which are disposed within the housing 3110. The auto-injector 3002 also includes a system actuator 3510, a compressed gas container 3412 and a gas release mechanism 3612.

The medicament injector 3210 includes a carrier 3250 that is movable within the housing 3110, a medicament container 3262 and a needle 3212. The medicament container 3262 is coupled to the carrier 3250. The needle 3212 is disposed within a needle hub portion 3223 (see FIG. 8) of the carrier 3250 to allow the needle to be placed in fluid communication with the medicament container 3262 during an injection event.

The movable member 3312 includes a proximal end portion 3316 and a distal end portion 3318. The proximal end portion 3316 includes a surface 3322 that, together with the housing 3110, defines a gas chamber 3120. Said another way, the surface 3322 defines a portion of a boundary of the gas chamber 3120. The distal end portion 3318 is disposed within the medicament container 3262. In use, the movable member 3312 moves towards the distal end portion 3114 of the housing 3110, as indicated by arrow C, in response to a force produced by a pressurized gas on the surface 3322 of the movable member 3312. As a result, the movable member 3312 and the medicament injector 3250 are moved towards the distal end portion 3114 of the housing 3110, thereby exposing the needle 3212 from the housing 3110. The movable member 3312 then continues to move within the medicament container 3262 to expel a medicament from the medicament container 3262 through the needle 3212.

The auto-injector 3002 is actuated by the system actuator 3510, which is configured to move the compressed gas container 3412 into contact with the gas release mechanism 3612. The gas release mechanism 3612 punctures a portion of the compressed gas container 3412 to release the pressurized gas contained therein into the gas chamber 3120 defined by the housing 3110.

The system actuator 3510 includes a rod 3540, a spring 3560 and a spring retainer 3570. The rod 3540 has a proximal end portion 3542 and a distal end portion 3544. The proximal end portion 3542 of the rod 3540 is coupled to the compressed gas container 3412. The distal end portion 3544 of the rod 3540 is coupled to the spring retainer 3570 by two projections 3548, which can be moved inwardly towards each other to decouple the rod 3540 from the spring retainer 3570, as discussed below.

The spring 3560 is disposed about the rod 3540 in a compressed state such that the spring 3560 is retained by the proximal end portion 3542 of the rod 3540 and the spring retainer 3570. In this manner, the rod 3540 is spring-loaded such that when the distal end portion 3544 of the rod 3540 is decoupled from the spring retainer 3570, the force of the spring 3560 causes the rod 3540, and therefore the compressed gas container 3412, to move proximally as indicated by arrow D and into contact with the gas release mechanism 3612.

The base 3520 defines an opening 3522 (shown in FIG. 13) configured to receive a portion of the projections 3548 when the base is moved towards the proximal end 3112 of the housing 3110, as indicated by arrow E. When the projections 3548 are received within the opening 3522, they are moved together causing the distal end portion 3544 of the rod 3540 to be released from the spring retainer 3570. In some embodiments, the opening 3522 extends though at least a portion of the base 3520. In some embodiments, the opening 3522 extends completely through the base 3520, for example, such that a locking portion of a safety guard (discussed in detail below) can be inserted through the opening.

As shown in FIGS. 4 and 5, the medicament injector 3210 defines a longitudinal axis Lm that is non-coaxial with the longitudinal axis Le defined by the compressed gas container 3412. Accordingly, the medicament injector 3210, the compressed gas container 3412 and the system actuator 3510 are arranged within the housing 3110 such that the housing has a substantially rectangular shape. Moreover, the non-coaxial relationship between the medicament injector 3210 and the compressed gas container 3412 allows the auto-injector 3002 to be actuated by manipulating the base 3520, which is located at the distal end portion 3114 of the housing 3110.

The use and actuation of the auto-injector 3002 includes several discrete operations. First, the auto-injector 3002 is enabled by removing the needle guard 3810 and the safety lock 3710 (see FIGS. 6 and 7). Second, the auto-injector 3002 is actuated by moving the base 3520 proximally towards the housing 3110. Third, when actuated, the compressed gas container 3412 engages the gas release mechanism 3612, which causes the pressurized gas to be released into the gas chamber 3120 (see FIG. 17). Fourth, the pressurized gas produces a force that causes the movable member 3312 and the medicament injector 3210 to move distally within the housing 3110 (see FIG. 23). The movement of the medicament injector 3210 causes the needle 3212 to extend from distal end portion 3114 of the housing 3110 and the base 3520. This operation can be referred to as the "needle insertion" operation. Fifth, when the medicament injector 3210 has completed its movement (i.e., the needle insertion operation is complete), the movable member 3312 continues to move the medicament container 3262 distally within the carrier 3250. The continued movement of the medicament container 3262 places the needle 3212 in fluid communication with the medicament container 3262, thereby allowing the medicament to be injected (see FIG. 29). Sixth, the force from the pressurized gas causes the movable member 3312 to move within the medicament container 3262, thereby expelling the medicament through the needle 3212 (see FIG. 30). This operation can be referred to as the "injection operation." Seventh, upon completion of the injection, the pressurized gas is released from the gas chamber 3120, thereby allowing the medicament injector 3210 and the movable member 3312 to be moved proximally within the housing. This operation can be referred to as the "retraction operation" (see FIG. 31). A detailed description of the components contained in the auto-injector 3002 and how they cooperate to perform each of these operations is discussed below.

Prior to use, the auto-injector 3002 must first be enabled by first removing the needle guard 3810 and then removing the safety lock, or locking member, 3710. As illustrated by arrow G in FIG. 6, the needle guard 3810 is removed by pulling it distally. Similarly, as illustrated by arrow H in FIG. 7, the safety lock 3710 is removed by pulling it substantially normal to the longitudinal axis Le of the compressed gas container 3412. Said another way, the safety lock 3710 is removed by moving it in a direction substantially normal to the direction that the needle guard 3810 is moved or to the longitudinal axis Lm of the needle (as shown in FIG. 5). As described in more detail herein, in some embodiments, the needle guard 3810 and the safety lock 3710 are cooperatively arranged to prevent the safety lock 3710 from being removed before the needle guard 3810 has been removed. Such an arrangement prevents the auto-injector 3002 from being actuated while the needle guard 3810 is in place.

Figure 8:
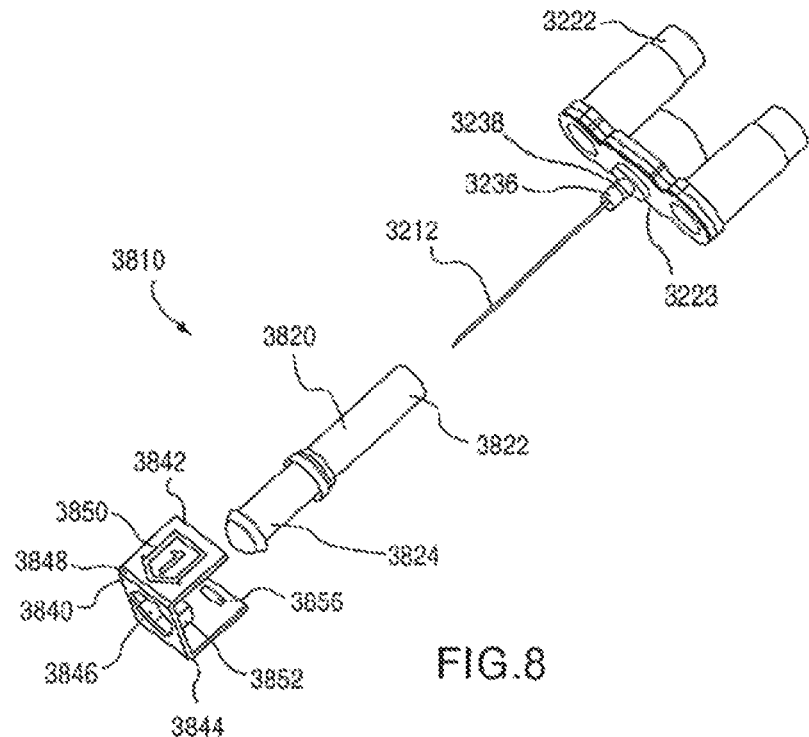
FIG. 8 is an exploded perspective view of a portion of the auto-injector illustrated in FIG. 6.
Figure 9:
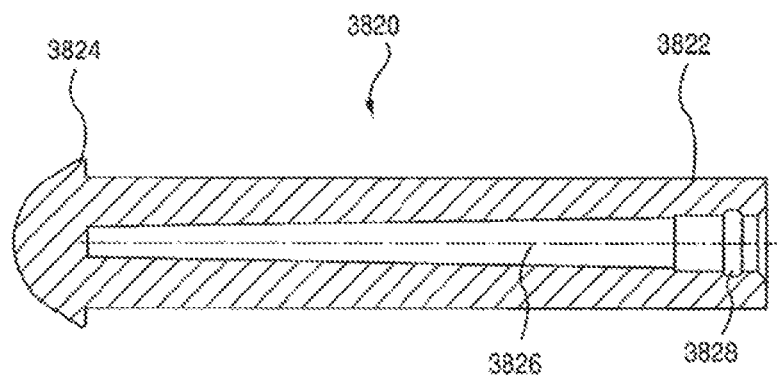
FIG. 9 is a cross-sectional view of a component illustrated in FIG. 8.
Figure 10:
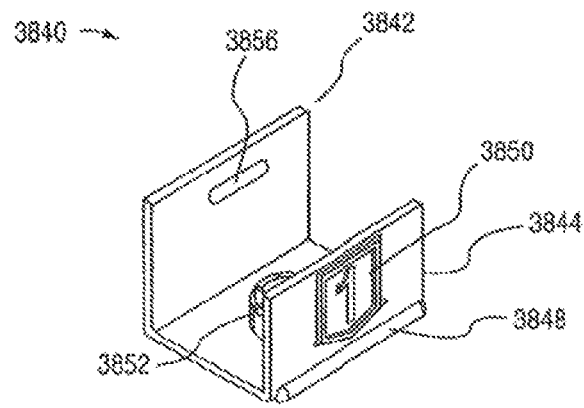
FIG. 10 is a perspective view of a component illustrated in FIG. 8.

As illustrated in FIGS. 8 and 9, the needle guard 3810 includes a sheath 3820 and a sheath retainer 3840. The sheath 3820 has a proximal end portion 3822 and a distal end portion 3824 and defines an opening 3826 configured to receive a portion of the needle 3212 when the needle guard 3810 is in a first (or installed) position. Said another way, the sheath 3820 is an inner member of the needle guard 3810 configured to substantially cover at least a portion of the needle 3212 when the needle guard is in a first position, and the sheath retainer 3840 is an outer member of the needle guard. The sheath 3820 further defines a recessed portion 3828 within the opening 3826 that engages a corresponding protrusion 3238 defined by an outer surface 3236 of the needle hub 3223. In this manner, when the needle guard 3810 is in its first position, the sheath 3820 is removably coupled to the needle hub 3223. In some embodiments, the recessed portion 3828 and the protrusion 3238 form a seal that is resistant to microbial penetration.

The sheath 3820 can be constructed from any suitable material. For example the sheath can be constructed from polyethylene, including high density polyethylene, polypropylene, polytetrafluoroethylene, thermoplastic polyurethane, rubber or any other elastomer or polymer. In some embodiments, the sheath 3820 is constructed from a rigid material. A rigid needle sheath can reduce the likelihood of needle sticks during the manufacturing process and can inhibit crumpling of the sheath around the needle during insertion of the needle into bodily tissue. In other embodiments, the sheath can be constructed from a flexible material. In some embodiments, the sheath 3820 is constructed from a material configured to resist or substantially prevent microbial penetration therethrough, and thus can maintain sterility of a needle received therein.

The sheath 3820 can be configured for use with one or more sterilization methods. In other words, the sheath can be configured to allow sterilization of the needle when the sheath is disposed over the needle and coupled to the needle hub. In some embodiments, the sheath 3820 is configured to allow a sterilant gas or other sterilizing agent to pass therethrough. For example, the sheath can include a valve configured to allow passage of the sterilant gas. In another example, the sheath is constructed of a porous material, such as a porous material configured to allow passage of the sterilant gas through the material while preventing microbes from passing therethrough.

The sheath retainer 3840 has a proximal portion 3842 and a distal portion 3844. The proximal portion 3842 of the sheath retainer 3840 includes a protrusion 3856 that engages a corresponding recess 3526 in the base 3520 (see FIG. 14) to removably couple the sheath retainer 3840 to the base 3520. The distal portion 3844 of the sheath retainer 3840 defines an opening 3846 through which the distal end portion 3824 of the sheath 3820 is disposed. The distal portion 3844 of the sheath retainer 3840 includes a series of retaining tabs 3852 that engage the distal end portion 3824 of the sheath 3820 to couple the sheath 3820 to the sheath retainer 3840. In this manner, when the sheath retainer 3840 is moved distally away from the base 3520 into a second (or removed) position, as shown in FIG. 6, the sheath 3820 is removed from the needle 3212. Moreover, this arrangement allows the sheath 3820 to be disposed about the needle 3212 independently from when the sheath retainer 3840 is coupled to the sheath 3820. As such, the two-piece construction of the needle guard provides flexibility during manufacturing, for example, because the sheath retainer can be installed after the sheath has been disposed about the needle and the needle sterilized. The distal portion 3844 of the sheath retainer 3840 also includes a protrusion 3848 to aid the user when grasping the needle guard 3810.

Figure 11:
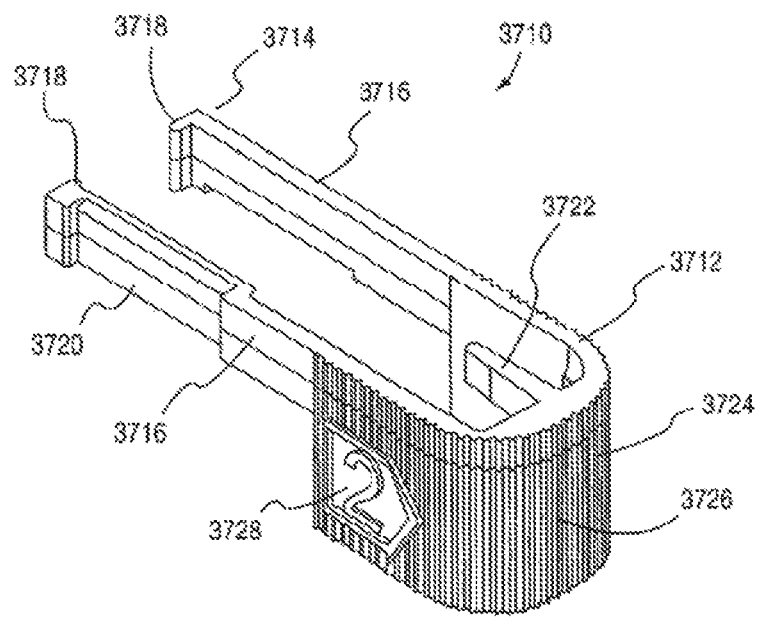
FIG. 11 is a perspective view of a member of the auto-injector illustrated in FIG. 7.

When the needle guard 3810 is in its first (or installed) position, the sheath retainer 3840 is disposed within a recess 3720 defined by one of the extended portions 3716 of the safety lock 3710 (see FIG. 11). This arrangement prevents the safety lock 3710 from being removed when the needle guard 3810 is in its first position, which in turn, prevents the auto-injector 3002 from being actuated when the needle guard 3810 is in its first position.

As illustrated in FIG. 8, the outer surface of the needle guard 3810 (or sheath retainer 3840 specifically) can include an indicia 3850 to instruct the user in operating an auto-injector. The indicia 3850 includes a numeral to indicate the order of operation and an arrow to indicate the direction in which the needle guard 3810 should be moved.

Figure 12:
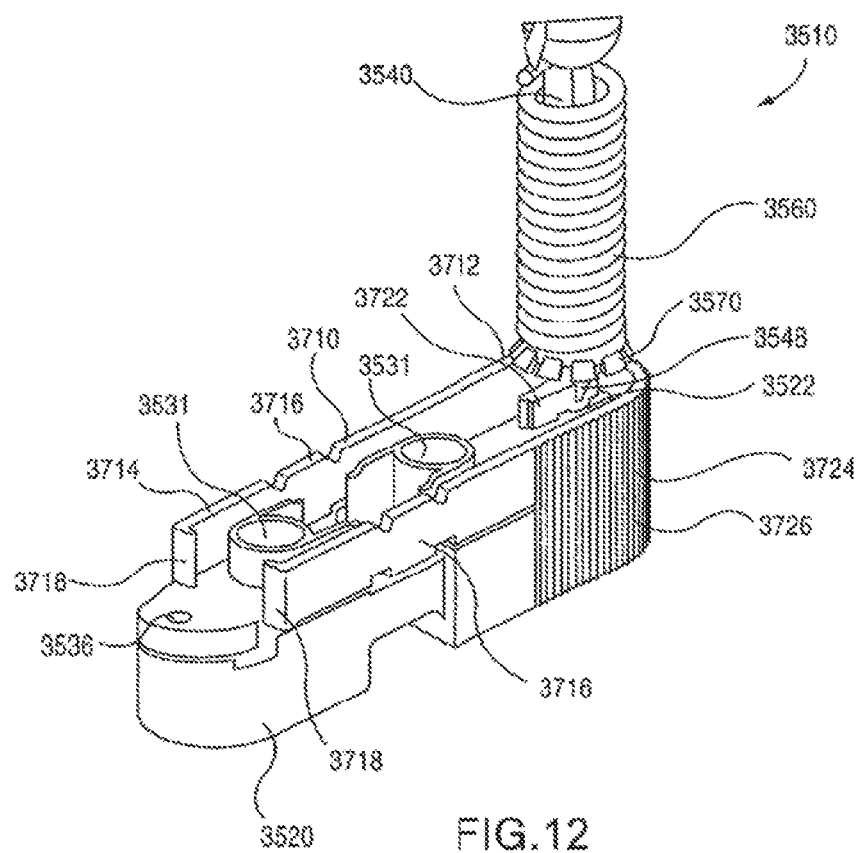
FIG. 12 is a perspective view of a portion of the auto-injector illustrated in FIGS. 3 and 7.

After the needle guard 3810 is removed, the user must then remove the safety lock 3710, as indicated in FIG. 7. As shown in FIG. 11, the safety lock 3710 is a U-shaped member having a first end 3712 and a second end 3714. The second end 3714 of the safety lock 3710 includes two extended portions 3716, each of which includes an inwardly facing protrusion 3718. When the safety lock 3710 is in its first (or locked) position, the extended portions 3716 extend around a portion of the base 3520 to space the base 3520 apart from the distal end portion 3114 of the housing 3110. As shown in FIG. 12, the protrusions 3718 are configured engage a portion of the base 3520 to removably couple the safety lock 3710 in its first position. One of the extended portions 3716 defines a recess 3720 that receives the sheath retainer 3840 when the needle guard 3810 is in its first position, as discussed above. Although only one extended portion 3716 is shown as including a recess 3720, in some embodiments both extended portions 3716 can include a recess 3720 to receive the sheath retainer 3840. The safety lock 3710 can be engaged with the needle guard 3810 to prevent movement of the safety lock 3710 when the needle guard 3810 is in place in any suitable manner. For example, in some embodiments, the sheath retainer includes protrusions that are received within corresponding openings defined by the safety lock. In some embodiments, the safety lock includes protrusions that are received within corresponding openings defined by the sheath retainer.

The first end 3712 of the safety lock 3710 includes a locking protrusion 3722 that extends inwardly. As shown in FIG. 12, when the safety lock 3710 is in its first position, the locking protrusion 3722 extends between the projections 3548 of the rod 3540 and obstructs an opening 3522 of the base 3520. In this manner, when the safety lock 3710 is in its first position, the base 3520 cannot be moved proximally to allow the projections 3548 to be received within the opening 3522. The arrangement of the locking protrusion 3722 also prevents the projections 3548 from being moved inwardly towards each other. Accordingly, when the safety lock 3710 is in its first position, the auto-injector 3002 cannot be actuated.

The outer surface 3724 of the first end 3712 of the safety lock 3710 includes a series of ridges 3726 to allow the user to more easily grip the safety lock 3710. The outer surface 3724 of the first end 3712 of the safety lock 3710 also includes an indicia 3728 to instruct the user in operating the auto-injector 3002. As shown in FIG. 11, the indicia 3728 includes a numeral to indicate the order of operation and an arrow to indicate the direction in which the safety lock 3710 should be moved. In some embodiments, the indicia 3728 can include different colors, detailed instructions or any other suitable indicia to instruct the user. In other embodiments, the indicia 3728 can protrude from the safety lock 3710 to aid the user when grasping the safety lock 3710.

Figure 13:
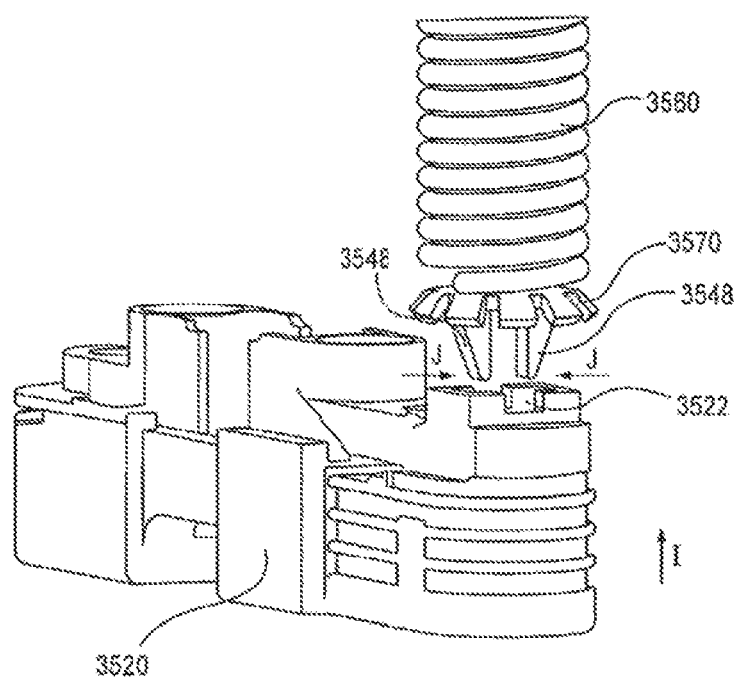
FIG. 13 is a perspective view of a portion of the auto-injector illustrated in FIGS. 3 and 12.
Figure 14:
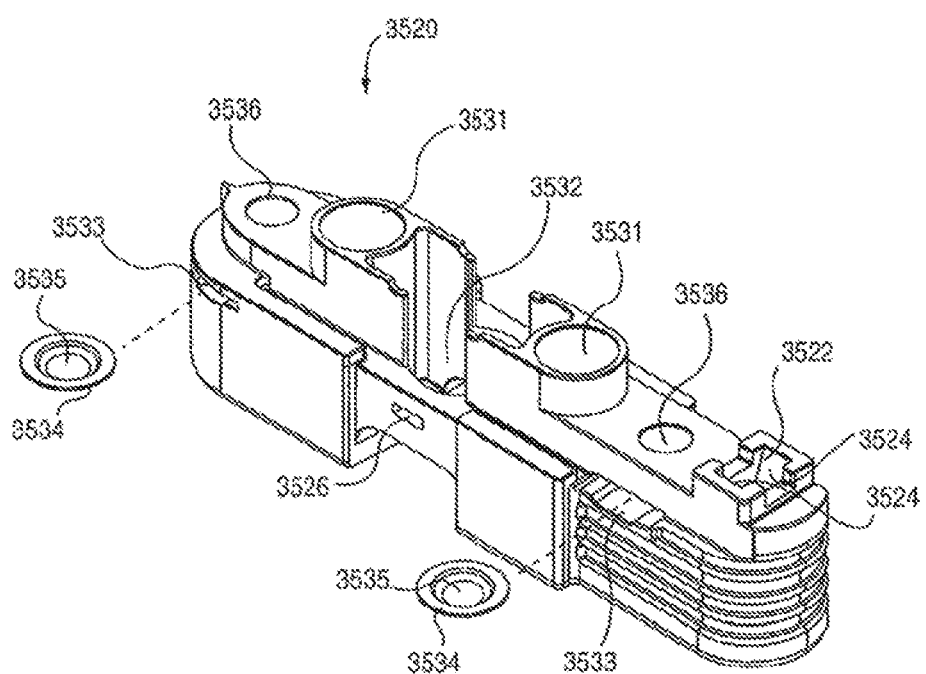
FIG. 14 is a partially exploded perspective view of a base of the auto-injector illustrated in FIG. 12.
Figure 22:
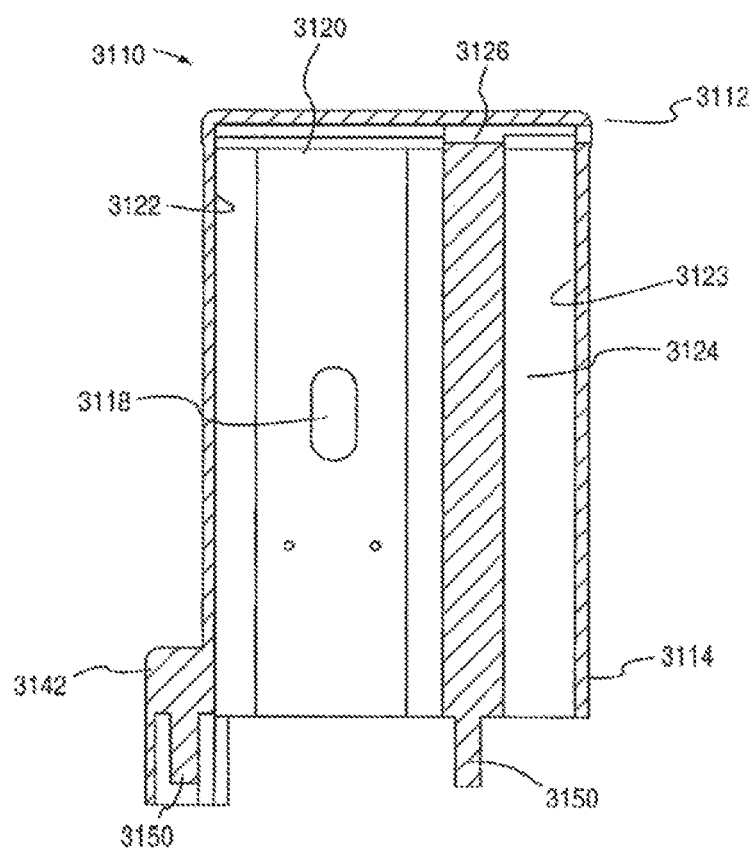
FIG. 22 is a cross-sectional view of the housing taken along line 22-22 in FIG. 21.

After being enabled, the auto-injector 3002 can then be actuated by moving the base 3520 proximally towards the housing 3110, as indicated by arrow I in FIG. 13. As shown in FIGS. 14 and 22, the base 3520 defines two openings 3536 that receive corresponding attachment protrusions 3150 disposed on the distal end portion 3114 of the housing 3110. In this manner, the movement and/or alignment of the base 3520 relative to the housing 3110 is guided by the attachment protrusions 3150 and the openings 3536 (see FIG. 22).

Each attachment protrusion 3150 is secured within its corresponding opening 3536 by a lock washer 3534. The lock washers 3534 each define an opening 3535 that receives a portion of the attachment protrusion 3150. The lock washers 3534 are disposed within slots 3533 defined by the base 3520 so that the openings 3535 are aligned with the attachment protrusions 3150. The openings 3535 are configured to allow the lock washers 3534 to move proximally relative to the attachment protrusions 3150, but to prevent movement of the lock washers 3534 distally relative to the attachment protrusions 3150. In this manner, when the attachment protrusions 3150 are disposed within the openings 3535 of the lock washers 3534, the base 3520 becomes fixedly coupled to the housing 3110. Moreover, after the base 3520 is moved proximally relative to the housing 3110, the lock washers 3534 prevent the base 3520 from returning to its initial position. Said another way, the arrangement of the lock washers 3534 prevents the base 3520 from being "kicked back" after the auto-injector 3002 has been actuated.

The base 3520 also defines a needle opening 3532, a recess 3526 and two retraction spring pockets 3531. The needle opening 3532 receives a portion of the needle guard 3810 when the needle guard is in its first position. Additionally, when the auto-injector is in its third configuration (see FIG. 23), the needle 3212 extends through the needle opening 3532. As described above, the recess 3526 receives the corresponding protrusion 3856 on the sheath retainer 3840 to removably couple the needle guard 3810 to the base 3520. As will be described in more detail herein, the retraction spring pockets 3531 receive a portion of the retraction springs 3350.

As shown in FIG. 14, the base 3520 includes two opposing tapered surfaces 3524 that define an opening 3522 configured to receive a corresponding tapered surface 3550 of the projections 3548 when the base is moved proximally towards the housing 3110. The opening 3522 can extend through the base 3520 or through at least a portion of the base. When the projections 3548 are received within the tapered opening 3522, they are moved together as indicated by arrows J in FIG. 13. The inward movement of the projections 3548 causes the rod 3540 to become disengaged from the spring retainer 3570, thereby allowing the rod 3540 to be moved proximally along its longitudinal axis as the spring 3560 expands. A more detailed description of the components included in the system actuator 3510 is provided below with reference to FIGS. 15 and 16.

The system actuator 3510 includes a rod 3540, a spring 3560 disposed about the rod 3540 and a spring retainer 3570. As described in more detail herein, the spring retainer 3570 retains both the spring 3560 and the rod 3540. The spring retainer 3570 includes a first surface 3572, a second surface 3574 and a series of outwardly extending engagement tabs 3576. The spring retainer 3570 is disposed within the gas container opening 3124 defined by the housing 3110 (see FIG. 22) such that the engagement tabs 3576 engage the interior surface 3123 of the housing 3110 to produce an interference fit. In this manner, the spring retainer 3570 is fixedly disposed within the housing 3110.

The rod 3540 has a proximal end portion 3542 and a distal end portion 3544. The distal end portion 3544 of the rod 3540 includes two extensions 3552 disposed apart from each other to define an opening 3554 therebetween. Each extension 3552 includes a projection 3548 having a tapered surface 3550 and an engagement surface 3549. When the rod 3540 is in its first (or engaged) position, the engagement surfaces 3549 engage the second surface 3574 of the spring retainer 3570 to prevent the rod 3540 from moving proximally along its longitudinal axis. As described above, when the base 3520 is moved proximally towards the housing 3110, the tapered surfaces 3550 of the projections 3548 cooperate with the corresponding tapered surfaces 3524 of the base 3520 to move the extensions 3552 inwardly towards each other. The inward motion of the extensions 3552 causes the engagement surfaces 3549 to become disengaged from the second surface 3574 of the spring retainer 3570, thereby allowing the rod 3540 to move between its first position to a second (or actuated) position.

The proximal end portion 3542 of the rod 3540 includes a retention portion 3545 having a first surface 3547 and a second surface 3546. The first surface 3547 of the retention portion 3545 engages the distal portion 3416 of the compressed gas container 3412. The second surface 3546 of the retention portion 3545 engages a proximal end 3562 of the spring 3560. Similarly, the first surface 3572 of the spring retainer 3570 engages a distal end 3564 of the spring 3560. In this manner, when the rod 3540 is in its first position, the spring 3560 can be compressed between the spring retainer 3570 and the retention portion 3545 of the rod 3540. Accordingly, when the rod 3540 is disengaged from the spring retainer 3570, the force imparted by the spring 3560 on the retention portion 3545 of the rod 3540 causes the rod 3540 to move proximally into its second position.

The proximal end portion 3542 of the rod 3540 is coupled to the compressed gas container 3412 by a connector 3580, which is secured to the distal end portion 3416 of the compressed gas container 3412 by a securing member 3588. The connector 3580 includes a proximal end portion 3582 and a distal end portion 3584. The distal end portion 3584 of the connector 3580 is disposed within the opening 3554 defined between the extensions 3552. In this manner, the connector 3580 is retained by the proximal end portion 3542 of the rod 3540. As will be described in more detail, the distal end portion 3584 of the connector 3580 includes locking tabs 3587.

The proximal end portion 3582 of the connector 3580 includes engagement portions 3586 that engage the distal end portion 3416 of the compressed gas container 3412. The engagement portions 3586 are coupled to the compressed gas container 3412 by the securing member 3588, which can be, for example, a shrink wrap, an elastic band or the like. In other embodiments, the engagement portions 3586 can produce an interference fit with the compressed gas container 3412, thereby eliminating the need for a securing member 3588.

Figure 17:
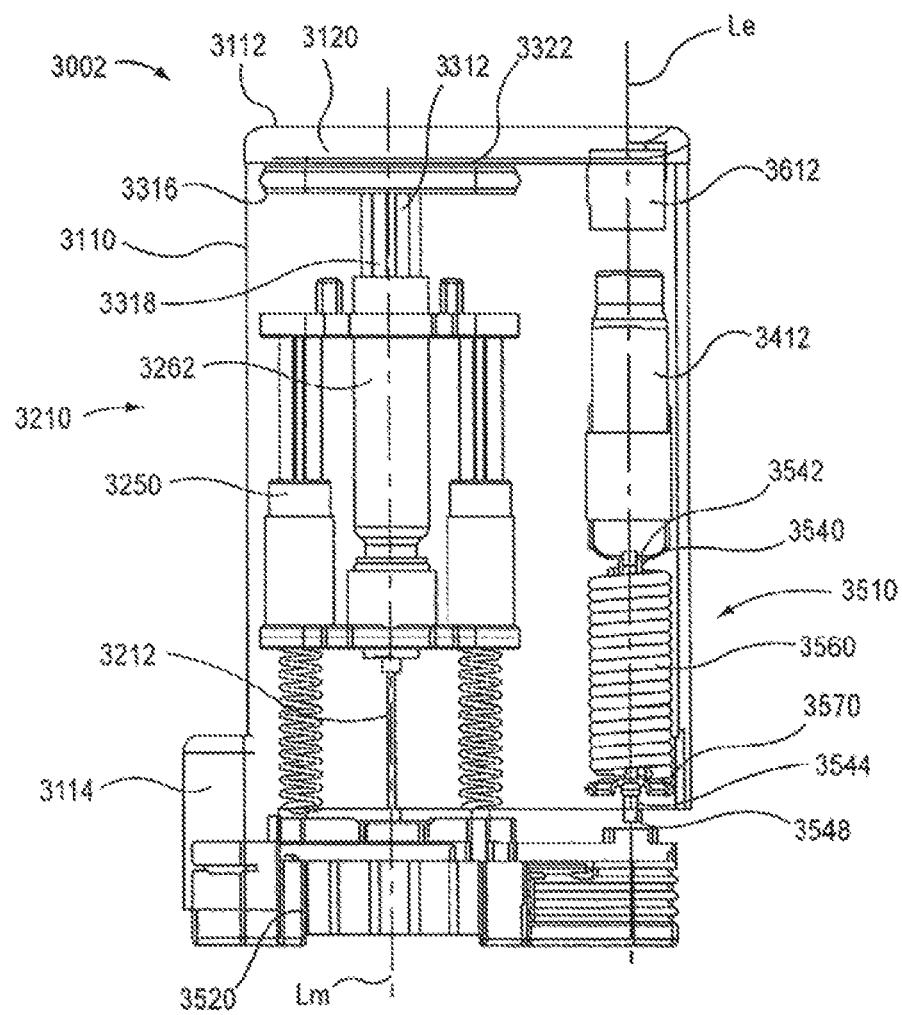
FIG. 17 is a front view of the auto-injector illustrated in FIG. 5 in a second configuration.

Because the rod 3540 is coupled to the compressed gas container 3412, when the rod 3540 is moved from its first (engaged) position to its second (actuated) position, the compressed gas container 3412 is moved proximally within the housing 3110 into engagement with the gas release mechanism 3612. FIG. 17 shows the auto-injector in a second configuration, in which the compressed gas container 3412 is engaged with the gas release mechanism 3612. When in the second configuration, the compressed gas contained within the compressed gas container 3412 is released to actuate the medicament injector 3210. A more detailed description of the gas release process is provided below with reference to FIGS. 18 through 22.

Figure 18:
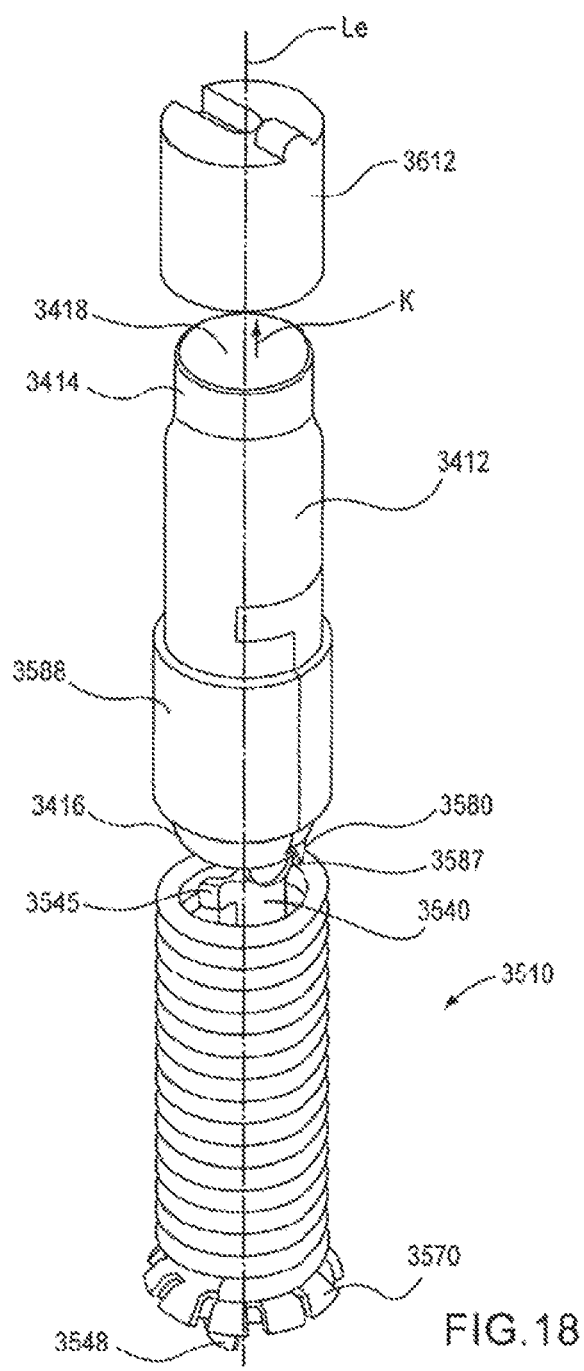
FIG. 18 is a perspective view of a portion of the auto-injector shown in FIG. 17.

FIG. 18 shows an exploded view of the system actuator 3510, the compressed gas container 3412 and the gas release mechanism 3612, each of which are disposed within the gas container opening 3124 defined by the housing 3110 (see FIG. 22). As shown, the compressed gas container 3412, the system actuator 3510 and the gas release mechanism 3612 are arranged substantially coaxial with each other. As previously discussed, when the auto-injector 3002 is actuated, the compressed gas container 3412 is moved proximally within the gas container opening 3124 defined by the housing 3110, as indicated by the arrow K in FIG. 18, until the proximal end 3414 of the compressed gas container 3412 engages the gas release mechanism 3612.

Figure 19:
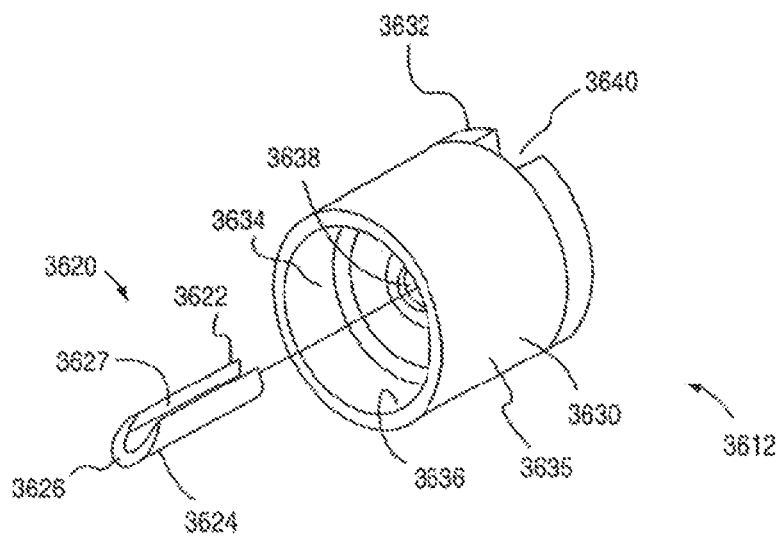
FIGS. 19 and 20 are perspective views of a portion of the auto-injector shown in FIG. 18.
Figure 20:
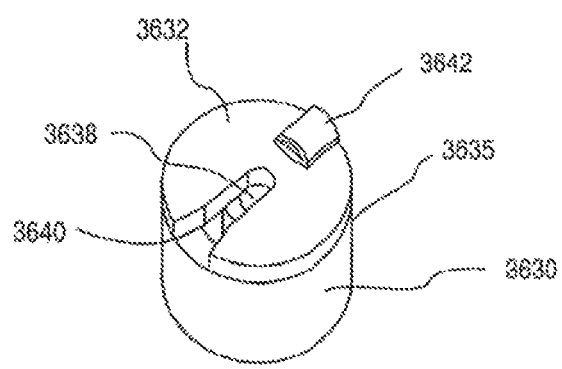
Figure 21:
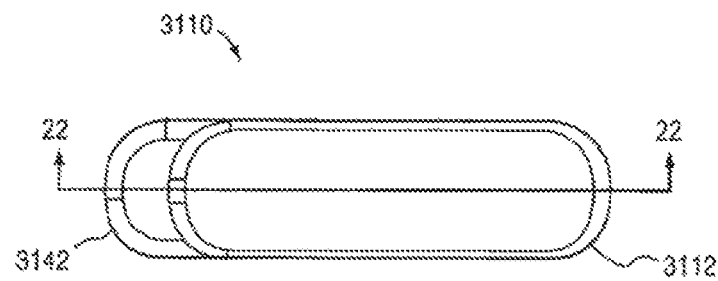
FIG. 21 is a top view of the housing of the auto-injector shown in FIG. 17.

As shown in FIGS. 19 and 20, the gas release mechanism 3612 includes a cap 3630 and a puncturing element 3620 coupled to and disposed within the cap 3630. The puncturing element has a proximal end 3622 and a distal end 3624. The distal end 3624 of the puncturing element 3620 defines a sharp point 3626 configured to puncture the proximal end 3414 of the compressed gas container 3412. The puncturing element 3620 defines an opening 3627 extending from its distal end 3624 to its proximal end 3622.

The cap 3630 has a proximal end 3632, an outer surface 3635 and an inner surface 3636. The inner surface 3636 of the cap 3630 defines an opening 3634 that receives the proximal end 3414 of the compressed gas container 3412 when the auto-injector 3002 is in its second configuration. The proximal end 3632 of the cap 3630 defines an opening 3638 therethrough and a channel 3640 in fluid communication with the opening 3638. The opening 3638 receives the proximal end 3622 of the puncturing element 3620 to couple the puncturing element 3620 to the cap 3630. The puncturing element 3620 is disposed within the cap 3630 such that when the compressed gas container 3412 is moved into the opening 3634, the distal end 3624 of the puncturing element 3620 punctures the proximal end 3414 of the compressed gas container 3412.

The cap 3630 is disposed within the gas container opening 3124 such that the outer surface 3635 of the cap 3630 engages the inner surface 3123 of the housing 3110. In some embodiments, the outer surface 3635 of the cap 3630 can be sized to produce an interference fit with the inner surface 3123 of the housing 3110. In other embodiments, the cap 3630 can be fixedly coupled within the gas container opening 3124 using an adhesive or any other suitable attachment mechanism.

The cap 3630 is oriented within the gas container opening 3124 so that the channel 3640 is aligned with and in fluid communication with the gas passageway 3126 defined by the housing 3110. Moreover, when oriented in this manner, the protrusion 3642 on the proximal end 3632 of the cap 3630 obstructs a portion of the gas passageway 3126, which can be manufactured as a through-hole, to fluidically isolate the gas passageway 3126 from an area outside of the housing 3110. After the proximal end 3414 of the compressed gas container 3412 has been punctured, pressurized gas flows from the compressed gas container 3412 into the gas passageway 3126 through the opening 3627 defined by the puncturing element 3620 and the channel 3640 defined by the proximal end 3632 of the cap 3630.

The inner surface 3636 of the cap 3630 is configured to hermetically seal the proximal end 3414 of the compressed gas container 3412 within the opening 3638. This arrangement prevents pressurized gas from leaking around the compressed gas container 3412 to an area outside of the housing 3110 after the proximal end 3414 of the compressed gas container 3412 has been punctured. In some embodiments, the inner surface 3636 is sized to produce an interference fit with the compressed gas container 3412. In other embodiments, the cap 3630 includes a separate sealing member, such as, for example, an o-ring, to seal the proximal end 3414 of the compressed gas container 3412 within the opening 3638.

Figure 15:
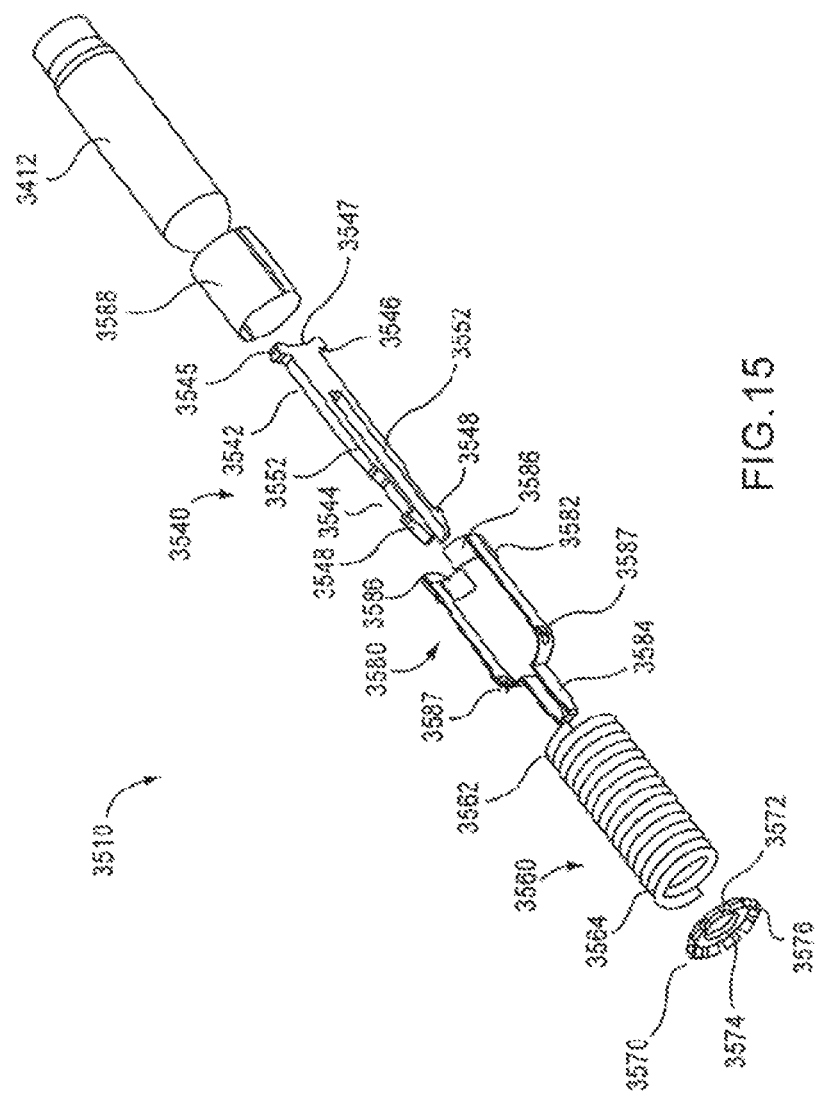
FIG. 15 is an exploded perspective view of a portion of the auto-injector shown in FIG. 4.
Figure 16:
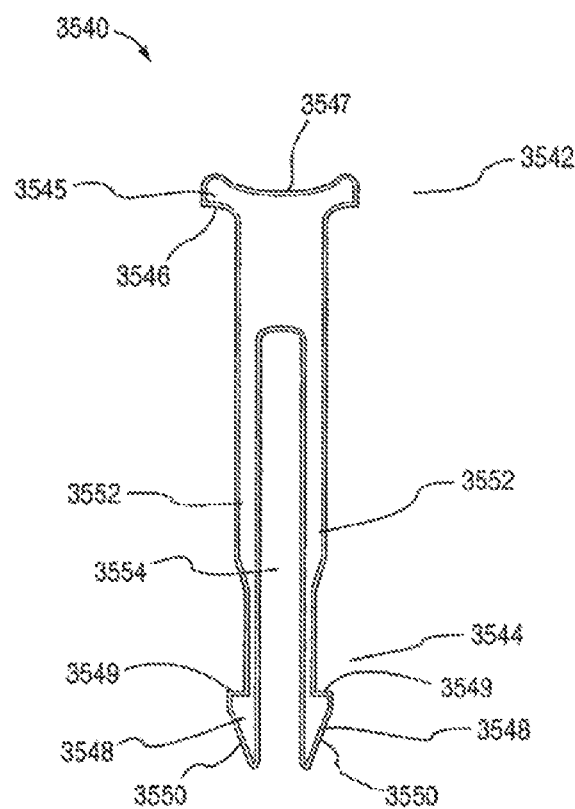
FIG. 16 is a front view of a component of the auto-injector shown in FIG. 15.

After the compressed gas container 3412 is moved into engagement with the gas release mechanism 3612, the position of the compressed gas container 3412 within the gas container opening 3124 is maintained by the locking tabs 3587 on the connector 3580. As shown in FIG. 15, each locking tab 3587 includes a pointed portion that is angled outwardly from the connector 3580. This arrangement allows the connector 3580 to move proximally within the gas container opening 3124 of the housing 3110, but prevents the connector 3580 from moving distally within the gas container opening 3124 of the housing 3110. Said another way, the arrangement of the locking tabs 3587 prevents the compressed gas container 3412 from being "kicked back" when exposed to the force produced by the pressurized gas as the pressurized gas is released.

Figure 23:
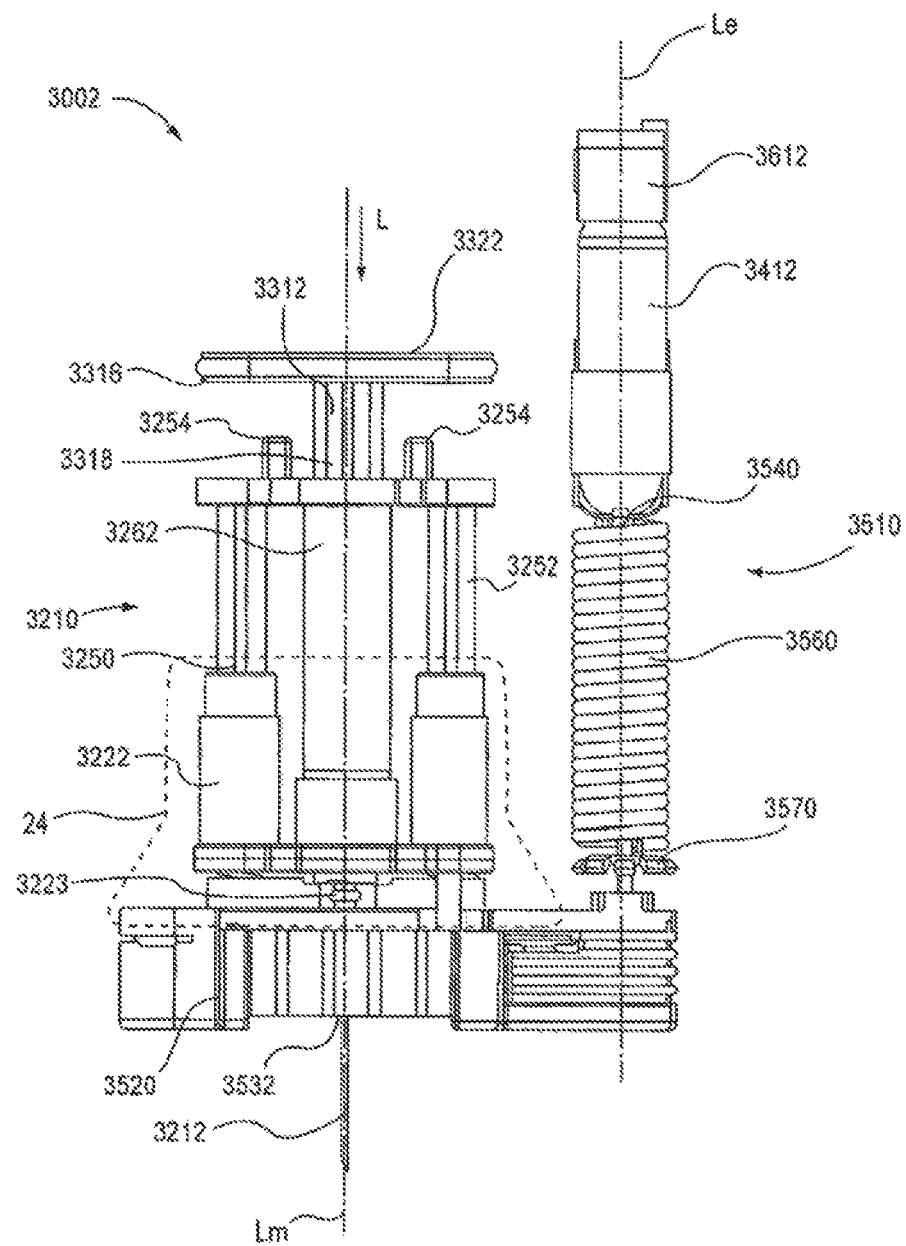
FIG. 23 is front view of the auto-injector illustrated in FIGS. 5 and 17 in a third configuration.
Figure 24:
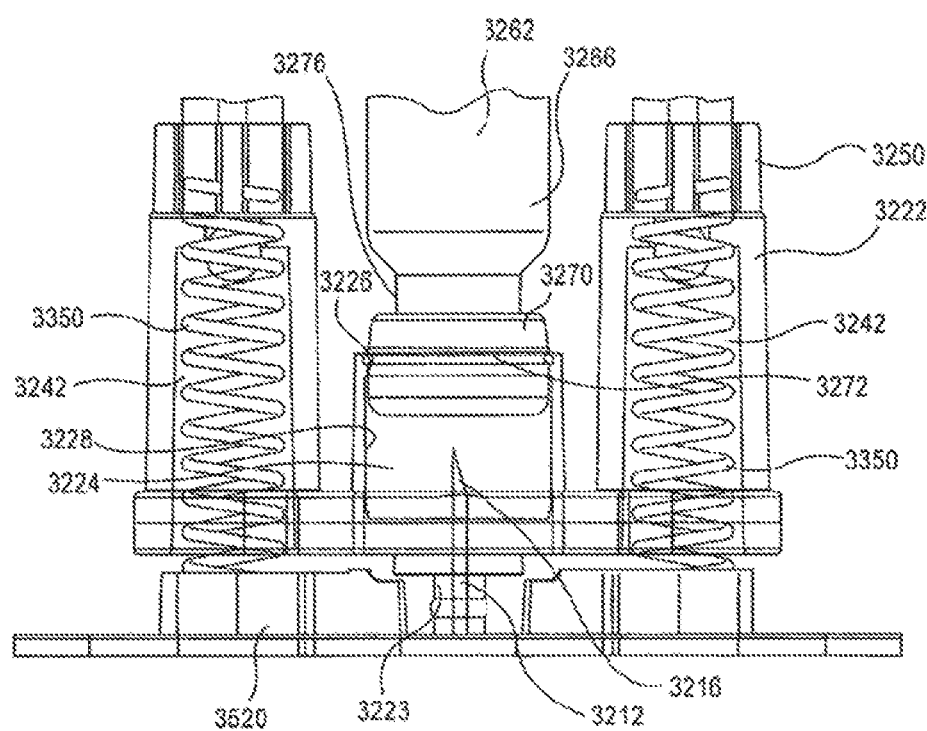
FIG. 24 is a front view of the portion of the auto-injector labeled as 24 in FIG. 23.

As previously discussed, the pressurized gas released from the compressed gas container 3412 produces a force on the boundary of the gas chamber 3120, including the surface 3322 of the movable member 3312. This force causes the movable member 3312 and the medicament injector 3210 move together distally within the housing 3110, as shown by arrow L, placing the auto-injector 3002 in a third configuration, as shown in FIG. 23. When in the third configuration, the distal end 3214 of the needle 3212 is disposed through the opening 3532 defined by the base 3520 to an area outside of the auto-injector 3002. Moreover, as shown in FIG. 24, when the auto-injector 3002 is in the third configuration, the proximal end 3216 of the needle 3212 remains spaced apart from the distal end 3266 of the medicament container 3210, ensuring that the needle 3212 remains fluidically isolated from the medicament container 3210. In this manner, the needle 3212 can be inserted into a patient as the auto-injector 3002 moves between its second configuration (FIG. 17) and its third configuration (FIG. 23) without injecting the medicament until after insertion is completed. A more detailed description of the medicament injector 3210 and the movable member 3312 is provided below with reference to FIGS. 23 through 28.

Figure 25:
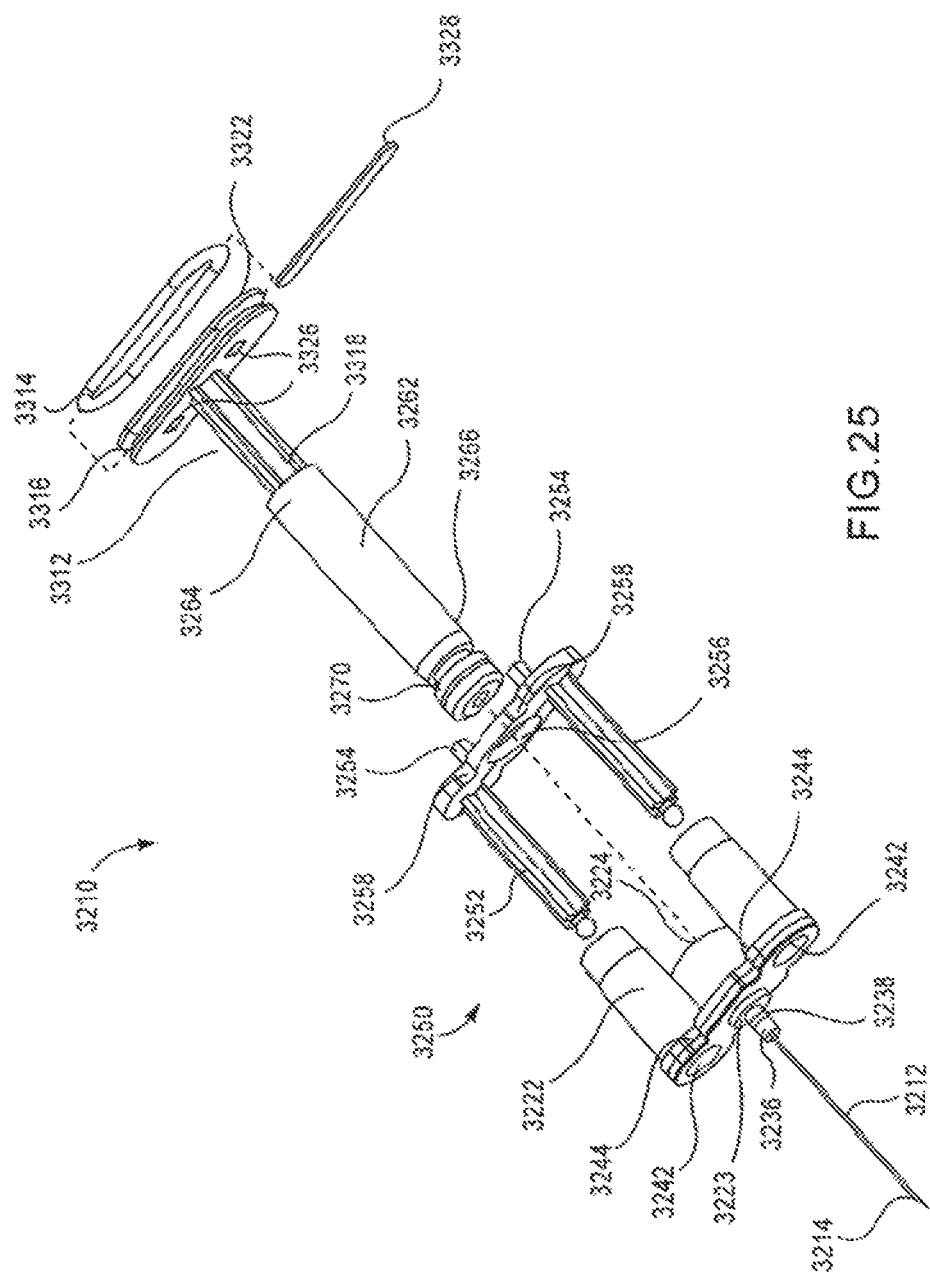
FIG. 25 is a perspective view of a portion of the auto-injector shown in FIG. 23.
Figure 26:
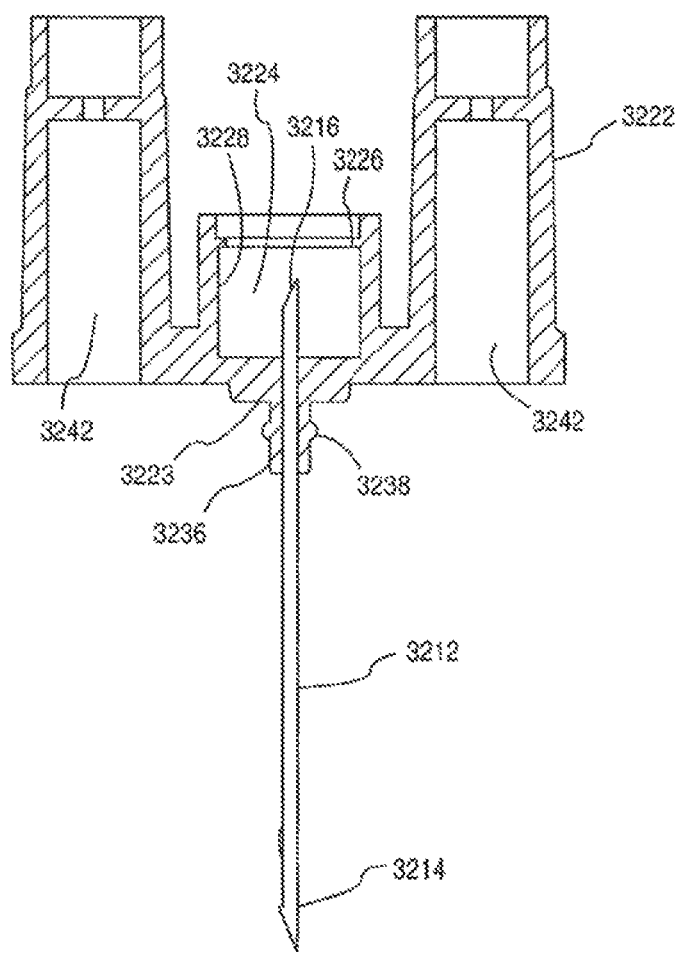
FIG. 26 is a cross-sectional view of a portion of the auto-injector as shown in FIG. 23.

As previously described, the medicament injector 3210 includes a carrier 3250, a medicament container 3262 and a needle 3212. The carrier 3250 has a lower portion 3222 and an upper portion 3252. The lower portion 3222 of the carrier 3250 includes a needle hub 3223, which contains the needle 3212. The lower portion 3222 of the carrier 3250 also defines an opening 3224 configured to receive a distal portion 3266 the medicament container 3262. As shown in FIG. 25, the needle 3212 is coupled to the needle hub 3223 such that the proximal end 3216 of the needle 3212 is disposed within the opening 3224 and the distal end 3214 of the needle 3212 extends distally outside of the needle hub 3223.

The inner surface 3228 of the lower portion 3222 defining the opening 3224 includes a protrusion 3226. The protrusion 3226 is configured to engage a corresponding recess 3272 defined by a sealing cap 3270 disposed at the distal portion 3266 of the medicament container 3262 (see FIG. 28) to secure the medicament container 3262 within the opening 3224 such that the proximal end 3216 of the needle 3212 is spaced apart from the distal end 3266 of the medicament container 3210. The protrusion 3226 and the recess 3272 are configured such that the protrusion 3226 will become disengaged from the recess 3272 when the force applied exceeds a predetermined value. Said another way, the protrusion 3226 and the recess 3272 collectively form a removable snap-fit that allows the medicament container 3262 to be moved within the opening 3224 when the force applied to the medicament container 3262 exceeds a predetermined value. This arrangement ensures that the needle 3212 remains fluidically isolated from the medicament container 3262 during the insertion operation.

The outer surface 3236 of the lower portion 3222 includes a protrusion 3238. As previously described, the protrusion 3238 is configured to engage a corresponding recess portion 3828 within the opening 3826 of the sheath 3820 (see FIG. 9) to removably couple the sheath 3820 to the needle hub 3223.

The lower portion 3222 of the carrier 3250 also defines two retraction spring pockets 3242 each receiving the proximal end 3352 of a retraction spring 3350. As previously discussed, the distal end 3354 of each retraction spring 3350 is retained within the retraction spring pockets 3531 defined by the base 3520. As shown in FIG. 24, when the carrier 3250 moves distally within the housing 3110, the retraction springs 3350 are compressed and therefore bias the carrier 3250 towards the proximal portion 3112 of the housing 3110.

The upper portion 3252 of the carrier 3250 defines an opening 3256 configured to receive a proximal portion 3264 of the medicament container 3262 and includes two valve actuators 3254. As described in more detail herein, the valve actuators 3254 are configured to engage a gas relief valve 3328 to allow the pressurized gas contained within the gas chamber 3120 to escape when the injection event is complete.

The upper portion 3252 of the carrier 3250 defines four gas relief passageways 3258. Similarly, the lower portion 3222 of the carrier 3250 defines four gas relief passageways 3244. When the pressurized gas is released from the gas chamber 3120, the gas relief passageways 3258, 3244 provide a fluid path to allow the pressurized gas to flow from the gas chamber 3120 to an area outside of the housing 3110.

Figure 28:
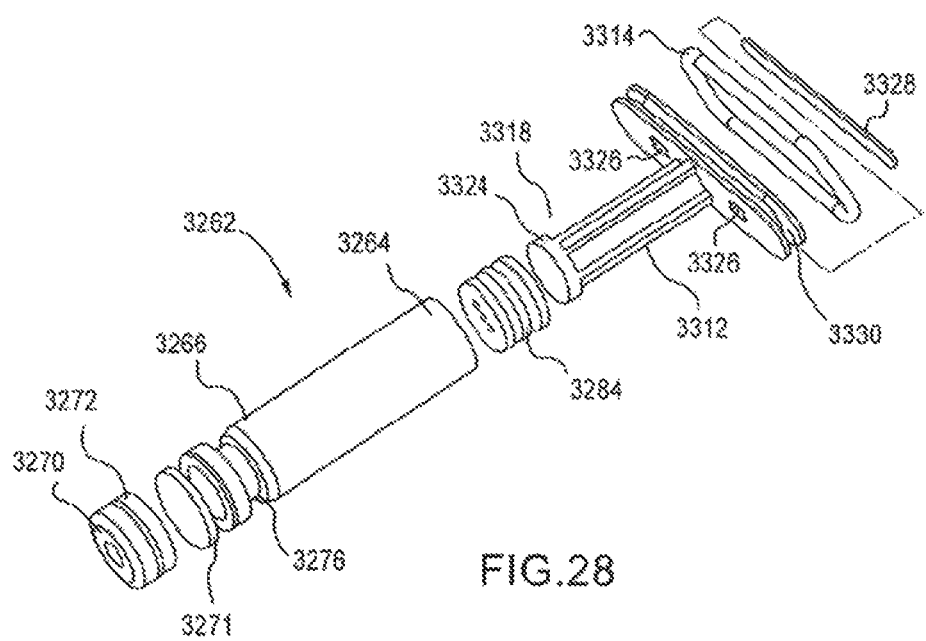
FIG. 28 is an exploded perspective view of a portion the auto-injector as shown in FIG. 23.

As described above, the movable member 3312 includes a proximal end portion 3316 and a distal end portion 3318. The distal end portion 3318 includes a piston 3324 disposed within the proximal portion 3264 of the medicament container 3262, such that the piston engages a plunger 3284 contained within the medicament container 3262, as shown in FIG. 28.

Figure 27:
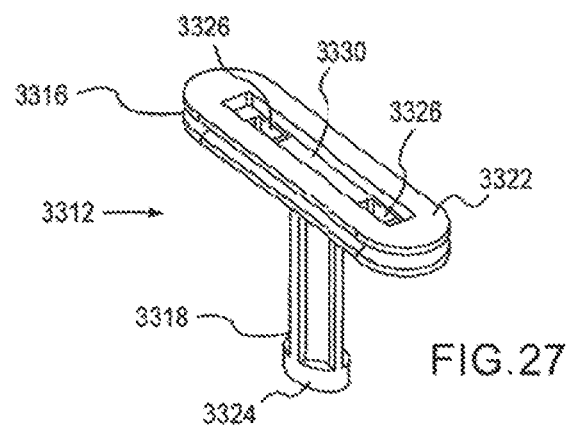
FIG. 27 is a perspective view of a portion of the auto-injector as shown in FIG. 23.

The proximal end portion 3316 includes a surface 3322 that defines a portion of a boundary of the gas chamber 3120. As shown in FIG. 27, the proximal end portion 3316 defines two openings 3326 therethrough, each of which are in fluid communication between the gas chamber 3120 and the interior of the housing 3110 outside the gas chamber 3120. The proximal end portion 3316 further defines a slot 3330 that receives a gas relief valve 3328, which can be, for example, a flexible rubber member. The gas relief valve 3328 is positioned within the slot 3330 and adjacent the openings 3326 to selectively allow fluid communication between the gas chamber 3120 and the area outside the gas chamber 3120 through the openings 3326. The operation of the gas relief valve 3328 is discussed in more detail herein.

The proximal end portion 3316 of the movable member 3312 also includes a seal 3314 that engages a portion the inner surface 3122 of the housing 3110 (see FIG. 22) to fluidically isolate the gas chamber 3120. Although the seal 3314 is shown as being an o-ring seal, in some embodiments, the seal need not be a separate component, but can rather be a portion of the proximal end portion 3316 of the movable member 3312.

Figure 29:
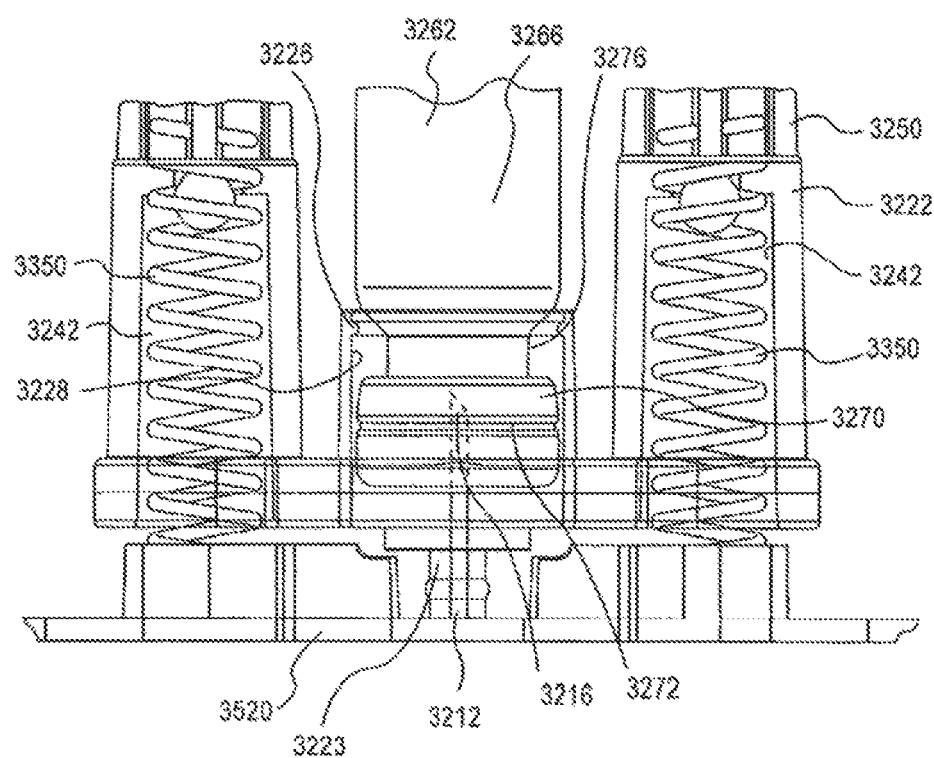
FIG. 29 is front view of the auto-injector illustrated in FIGS. 5, 17 and 24 in a fourth configuration.

When the needle insertion operation is completed, the lower portion 3222 of the carrier 3250 engages the base 3520, preventing further distal movement of the carrier 3250 within the housing. Because the distal motion of the carrier 3250 is opposed, the force exerted by the pressurized gas on the surface 3322 of the movable member 3312 increases until the protrusion 3226 of the lower portion 3222 of the carrier 3250 and the recess 3272 defined by sealing cap 3270 of the medicament container 3262 become disengaged. Accordingly, the medicament container 3262 to moves distally relative to the carrier 3250, placing the auto-injector 3002 in a fourth configuration, as shown in FIG. 29. When moving between the third configuration (FIG. 24) and the fourth configuration (FIG. 29), the proximal end 3216 of the needle 3212 pierces the liner 3271 within the sealing cap 3270 disposed at the distal portion 3266 of the medicament container 3262. As such, when in the fourth configuration, the proximal end 3216 of the needle 3212 is in fluid communication with the medicament container 3262, thereby allowing the medicament to be injected.

Figure 30:
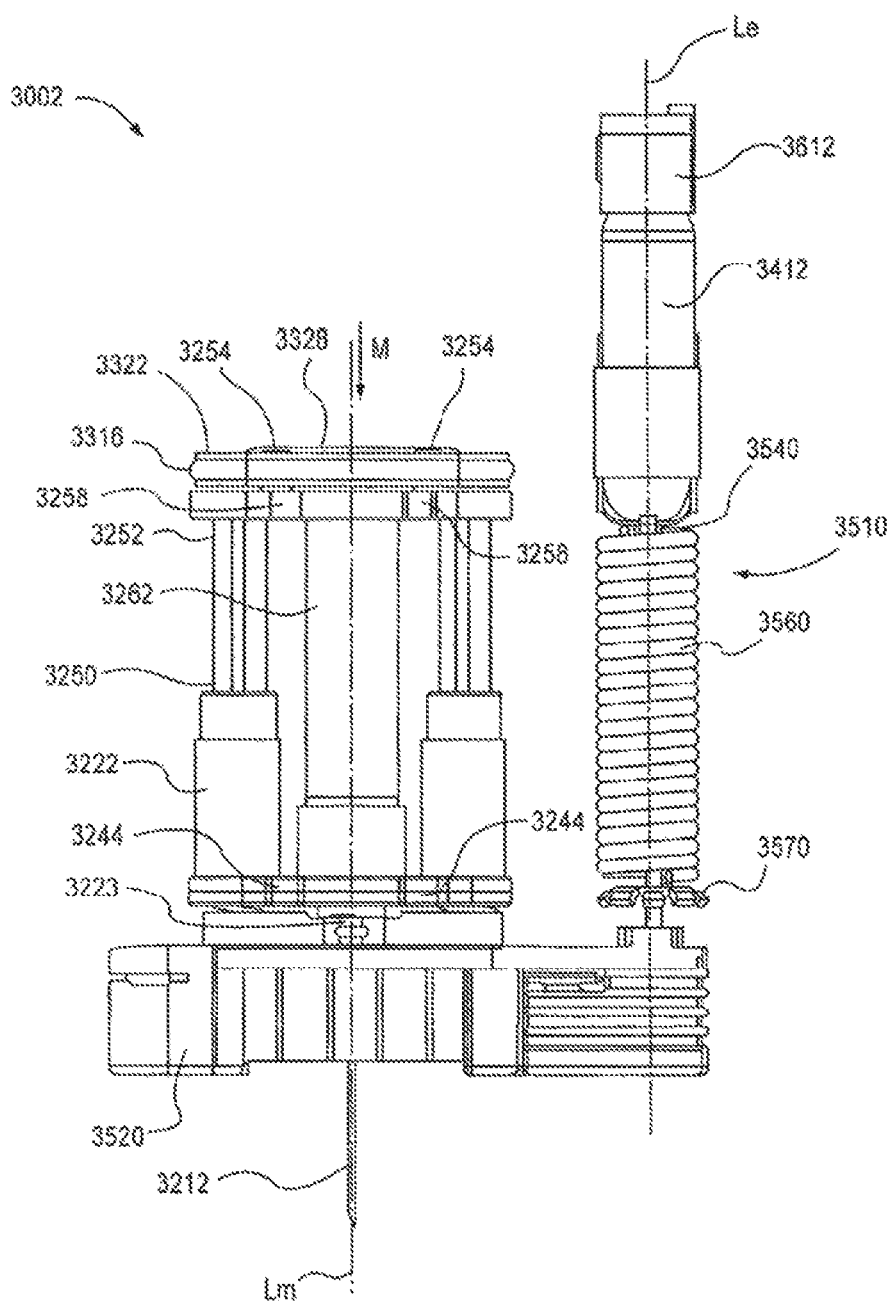
FIG. 30 is a front view of a portion of the auto-injector illustrated in FIGS. 5, 17, 24 and 29 in a fifth configuration.

Once the needle 3212 is in fluid communication with the medicament container 3262, the force from the pressurized gas causes the piston 3324 of the movable member 3312 to move the plunger 3284 within the medicament container 3262, as shown by arrow M in FIG. 30, thereby expelling the medicament through the needle 3212. The piston 3324 and the plunger 3284 move a predetermined distance within the medicament container 3262, placing the auto-injector 3002 in a fifth configuration, as shown in FIG. 30. When the auto-injector 3002 is in the fifth configuration, the injection of medicament is complete.

When the auto-injector 3002 is in its fifth configuration, proximal portion 3316 of the movable member 3312 is in contact with the upper portion 3252 of the carrier 3250, thereby preventing further movement of the piston 3324 within the medicament container 3262. In this manner, the distance through which the piston 3324 travels, and therefore the amount of medicament injected, can be controlled.

Additionally, when the auto-injector 3002 is in its fifth configuration, the valve actuators 3254 are disposed within the openings 3326 such that the valve actuators 3254 displace the gas relief valve 3328. Accordingly, the pressurized gas contained within the gas chamber 3120 can flow from the gas chamber 3120 to the area within the housing 3310 outside of the gas chamber 3310. As previously discussed, the gas relief passageways 3258, 3244 provide a fluid path to allow the pressurized gas to flow from the gas chamber 3120, through the opening 3532 defined by the base 3520 and to an area outside of the housing 3110.

Figure 31:
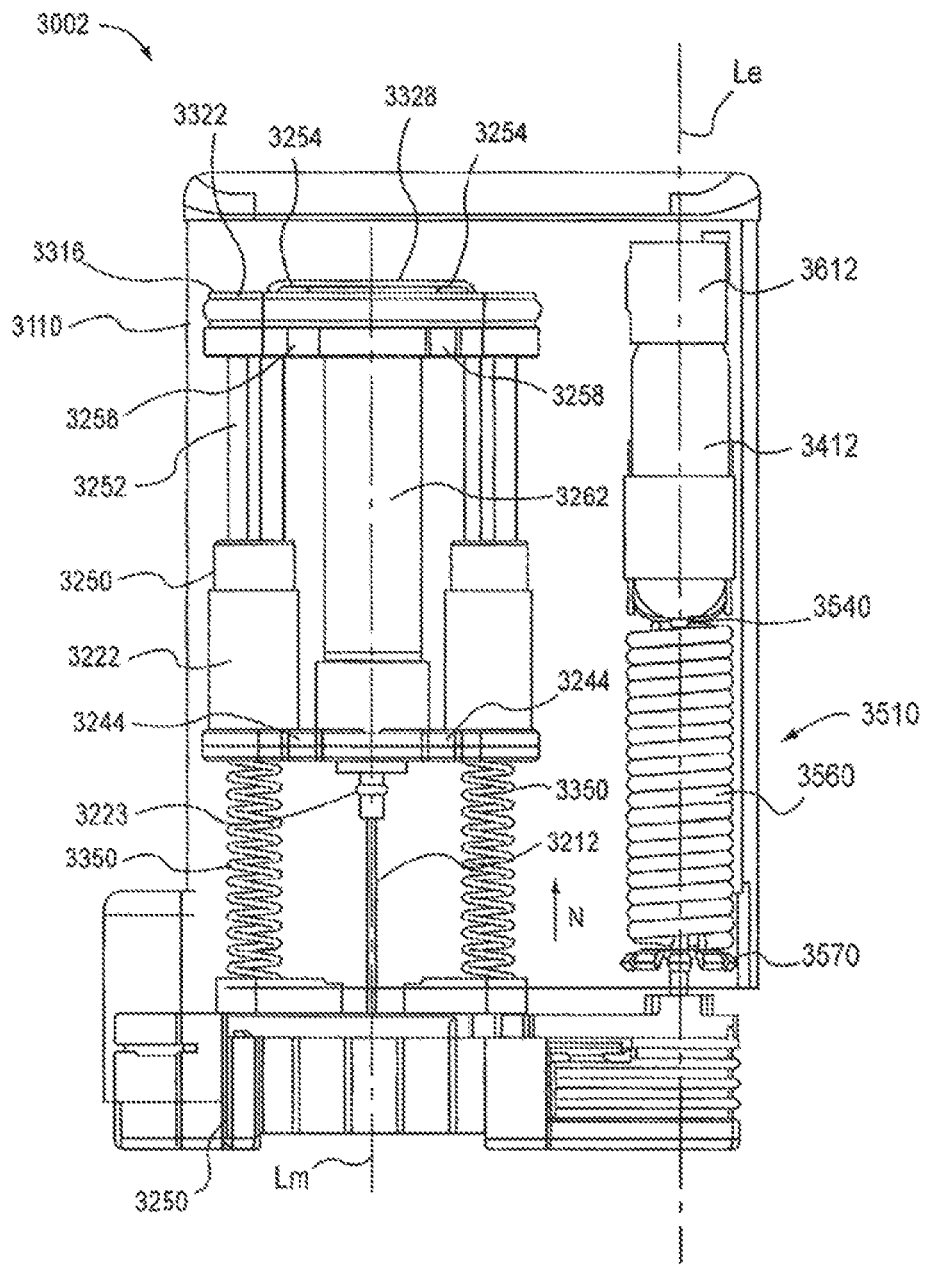
FIG. 31 is a front view of the auto-injector illustrated in FIGS. 5, 17, 24, 29 and 30 in a sixth configuration.

When the pressurized gas flows out of the gas chamber 3120, the pressure exerted on the surface 3322 of the movable member 3312 decreases. Accordingly, the force exerted by the retraction springs 3350 is sufficient to move the medicament injector 3210 and the movable member 3312 proximally within the housing 3110, as shown by arrow N, into a sixth (or retracted) configuration as shown in FIG. 31. Because the medicament injector 3210 and the movable member 3312 move together, the valve actuators 3254 remain disposed within the openings 3326 as the auto-injector 3002 moves into the sixth configuration. In this manner, the gas relief valve 3328 remains displaced and the openings 3326 remain in fluid communication with the gas chamber 3120 and the area within the housing 3310 outside of the gas chamber 3310 independent of the position of the movable member 3312. Such an arrangement ensures that all of the pressurized gas flows out of the gas chamber 3120, thereby ensuring that the medicament injector 3210 and the movable member 3312 return to the sixth configuration and do not oscillate between the sixth configuration and the fifth configuration, which could lead to the needle 3212 not being fully retracted into the housing 3110.

Although the auto-injector 3002 has been shown and described having a housing 3110 having a substantially rectangular shape, in some embodiments, an auto-injector can have a housing having any shape. In some embodiments, for example, an auto-injector can have a substantially cylindrical shape. In other embodiments, for example, the auto-injector can have an irregular and/or asymmetrical shape.

Figure 32:
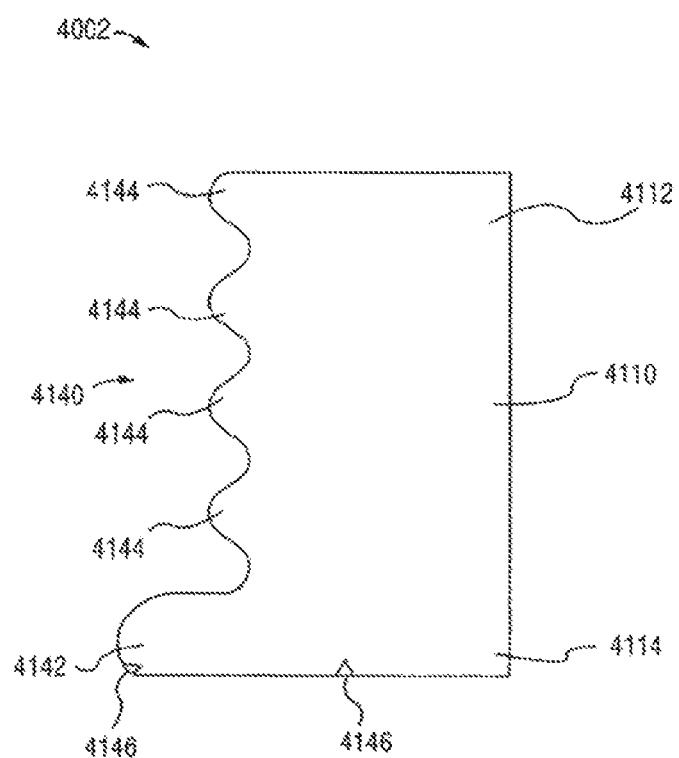
FIG. 32 is a front view of an auto-injector according to an embodiment of the invention.

Although the auto-injector 3002 has been shown and described as including a protrusion 3142 disposed at the distal end portion 3114 of the housing 3110 to help a user grasp and retain the housing 3110, in some embodiments, a protrusion can be disposed anywhere along the housing. In other embodiments, a protrusion can symmetrically surround the distal portion of the housing. In yet other embodiments, the housing of an auto-injector can include a gripping portion configured to help a user grasp and retain the housing. The gripping portion can include, for example, a textured surface, a contoured surface, a surface having an adhesive that forms a tacky surface to adhere to the user's hand or the like. For example, FIG. 32 shows an auto-injector 4002 according to an embodiment of the invention having a housing 4110. The housing 4110 includes a proximal end portion 4112, a distal end portion 4114 and a gripping portion 4140. The distal end portion 4114 of the housing 4110 includes a protrusion 4142 to prevent the user's hand from slipping off of the distal end portion 4114 of the housing 4110 when using the auto-injector 4002. Similarly, the gripping portion 4140 includes a series of contours 4144 that engage the user's fingers to help the user grasp and retain the housing 4110 when the auto-injector 4002 is in use.

The distal end portion 4114 of the housing 4110 also includes two alignment marks 4146 to guide the user when placing the auto-injector 4002 against the body. Although the alignment marks 4146 are shown as markings on the housing 4110, in other embodiments, the alignment marks can include protrusions, openings or the like.

Certain components of the auto-injector 3002 are shown and described as being coupled together via protrusions and mating recesses. The protrusions and/or recesses can be disposed on any of the components to be coupled together and need not be limited to only a certain component. For example, the base 3520 is shown as defining two openings 3536 that receive corresponding attachment protrusions 3150 on the distal end portion 3114 of the housing 3110. In some embodiments, however, the protrusions can be disposed on the base and the mating recesses can be defined by the distal end portion of the housing. In other embodiments, two or more components can be coupled together in any suitable way, which need not include protrusions and mating recesses. For example, in some embodiments, two or more components can be coupled together via mating shoulders, clips, adhesive and the like.

Similarly, although certain components of the auto-injector 3002 are shown and described as being constructed from multiple separate components, in some embodiments, such components can be monolithically constructed. For example, the carrier 3250 is shown and described as including an upper portion 3252 and a lower portion 3222 that are constructed separately and then coupled together. In other embodiments, a carrier can be constructed monolithically.

Although the sheath retainer 3840 of the auto-injector 3002 has been shown and described as including a protrusion 3856 that engages a corresponding recess 3526 in the base 3520 to removably couple the sheath retainer 3840 to the base 3520, in some embodiments, the sheath retainer can include a protrusion configured to engage a different corresponding recess on the auto-injector 3002. For example, the sheath retainer can include a protrusion configured to engage a corresponding recess in the distal end portion 3114 of the housing 3110.

Although the safety lock (or locking member) 3710 of the auto-injector 3002 has been shown and described as including a protrusion 3718 configured to engage a base 3520 movably coupled to the housing 3110, in some embodiments, the safety lock can include a protrusion configured to engage a different portion of the auto-injector 3002. For example, the safety lock can include a protrusion configured to engage a portion of the housing 3110, such as the distal end portion 3114 of the housing 3110, to removably couple the safety lock in its first position.

Although the base 3520 of the auto-injector 3002 has been shown and described covering almost the entire distal end portion 3114 of the housing 3110, in some embodiments, a base configured to actuate the auto-injector can be disposed about only a portion of the distal end of the housing. For example, in some embodiments, an auto-injector can include a button extending from the distal end portion of the housing configured to engage and release the system actuator.

Although the rod 3540 is shown and described as being an elongated member that is released by being elastically deformed, in some embodiments, a rod can be of any suitable shape and in any suitable orientation within the housing. Moreover, in some embodiments, a rod can be released by being plastically deformed. For example, in some embodiments, a rod can be disposed along an axis that is offset from the longitudinal axis of the energy storage member. In some embodiments, the rod can be configured to break upon actuation.

Although the gas release mechanism 3612 is shown and described as including a puncturing element 3620 to puncture a portion of the compressed gas container 3262, the gas release mechanism 3612 need not include a puncturing element 3620. For example, in some embodiments, the gas release mechanism can include an actuator configured to actuate a valve that controls the flow of gas out of the compressed gas container. For example, in some embodiments, a compressed gas container can include a spring loaded check ball and the gas release mechanism can include an actuator configured to engage and depress the check ball to release pressurized gas from the compressed gas container.

Although the distance through which the piston 3324 travels, and therefore the amount of medicament injected, is shown and described as being controlled by configuring the movable member 3312 such that it is in contact with the upper portion 3252 of the carrier 3250 when the auto-injector 3002 is in its fifth configuration, in other embodiments, any suitable method of controlling the piston travel can be employed. For example, in some embodiments, piston travel can be limited by including a protrusion within the medicament container, such as a necked portion, that limits the motion of the piston within the medicament container. In other embodiments, the housing can include a protrusion to limit the motion of the movable member. In yet other embodiments, the valve actuator can be configured to actuate the gas relief valve when the piston has moved a predetermined distance within the medicament container. In yet other embodiments, a combination of each of the above methods for controlling the piston travel can be employed.

Although the auto-injector 3002 is shown and described as having six different configurations that are different from each other, in some embodiments, certain configuration of an auto-injector can be the same as another configuration. For example, in some embodiments, a "pre-actuation configuration can be the same as a "retracted" configuration. In other embodiments, any of the functions described above can be accomplished when an auto-injector is moved between any number of different configurations.

Figure 33:
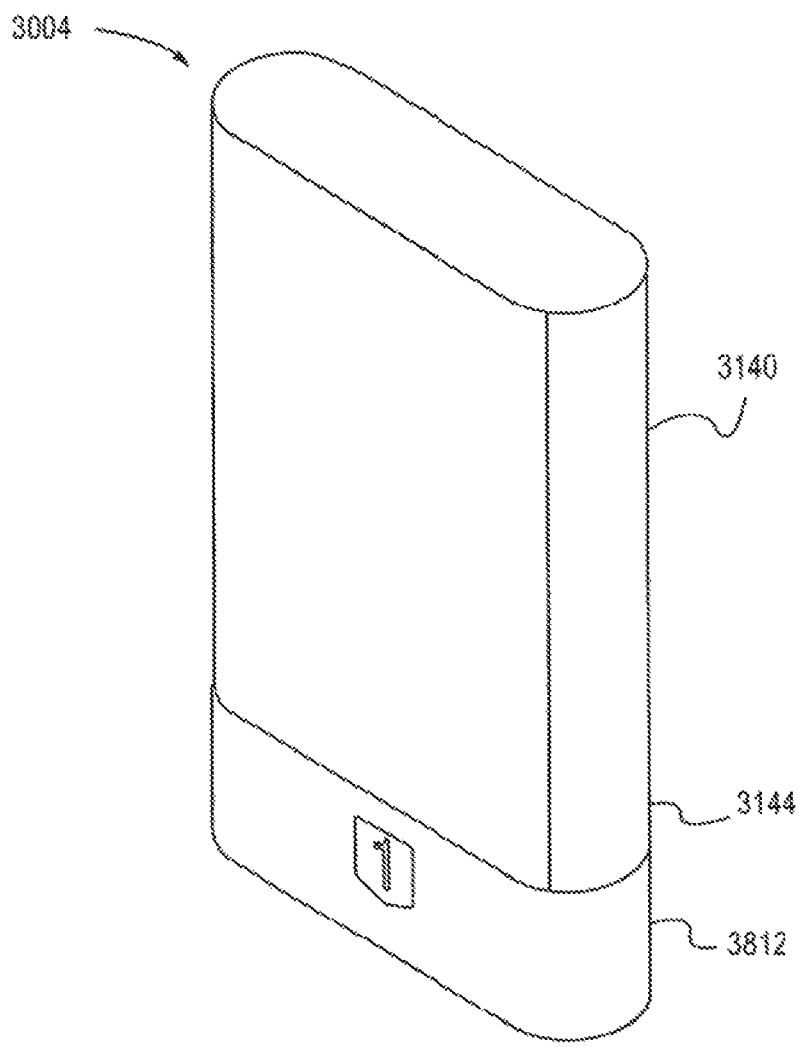
FIGS. 33 and 34 are perspective views of an auto-injector according to an embodiment of the invention in a first configuration and a second configuration respectively.
Figure 34:
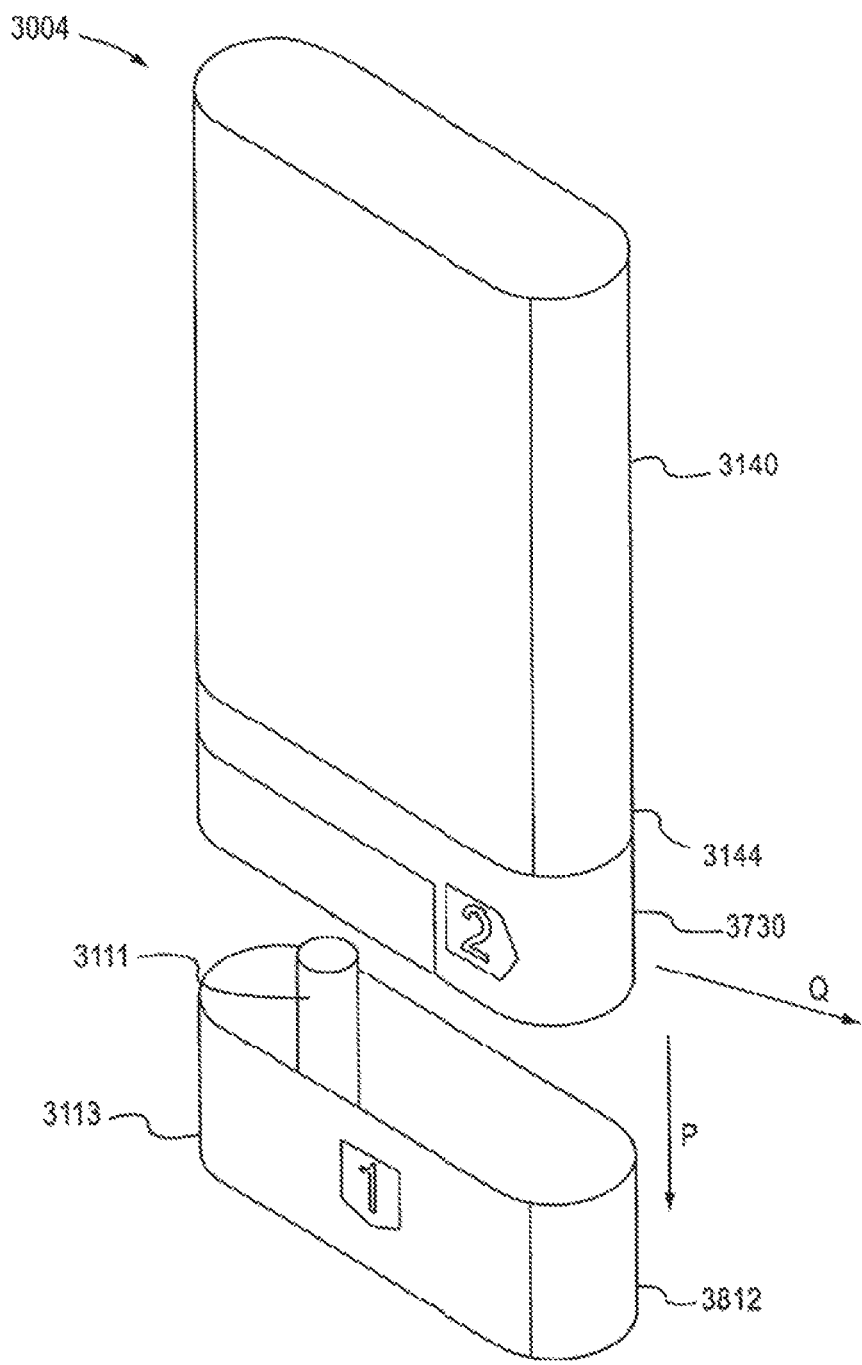

In some embodiments, as illustrated in FIGS. 33-34, an auto-injector 3004 includes a housing 3140 and a needle guard 3812 removably coupled to the distal end portion 3144 of the housing 3140. The needle guard 3812 includes a sheath 3111 and a sheath retaining portion 3113. The needle guard 3812 has a first position and a second position. In its first position, the needle guard 3812 is coupled to the housing 3140. For example, the sheath retaining portion 3113 of the needle guard 3812 is configured to substantially cover or encase the distal end portion 3144 of the housing 3140 when the needle guard is in its first position. In its second position, the needle guard 3812 is removed from the housing 3140. The sheath 3111 is coupled to the sheath retaining portion 3113 similar to the coupling of the sheath 3820 and sheath retainer 3840 as described in detail above with reference to FIG. 8. As such, as the sheath retaining portion 3113 is moved distally in the direction of arrow P, the sheath 3111 is also moved distally and removed from the housing 3140. Once the needle guard 3812 is moved to its second (or removed) position, the safety lock 3730 is accessible. The safety lock 3730 is removed from the housing 3140 by pulling the safety lock in a direction that is substantially normal to the direction in which the needle guard 3812 is removed, such as in the direction of arrow Q as illustrated in FIG. 34.

Figure 35:
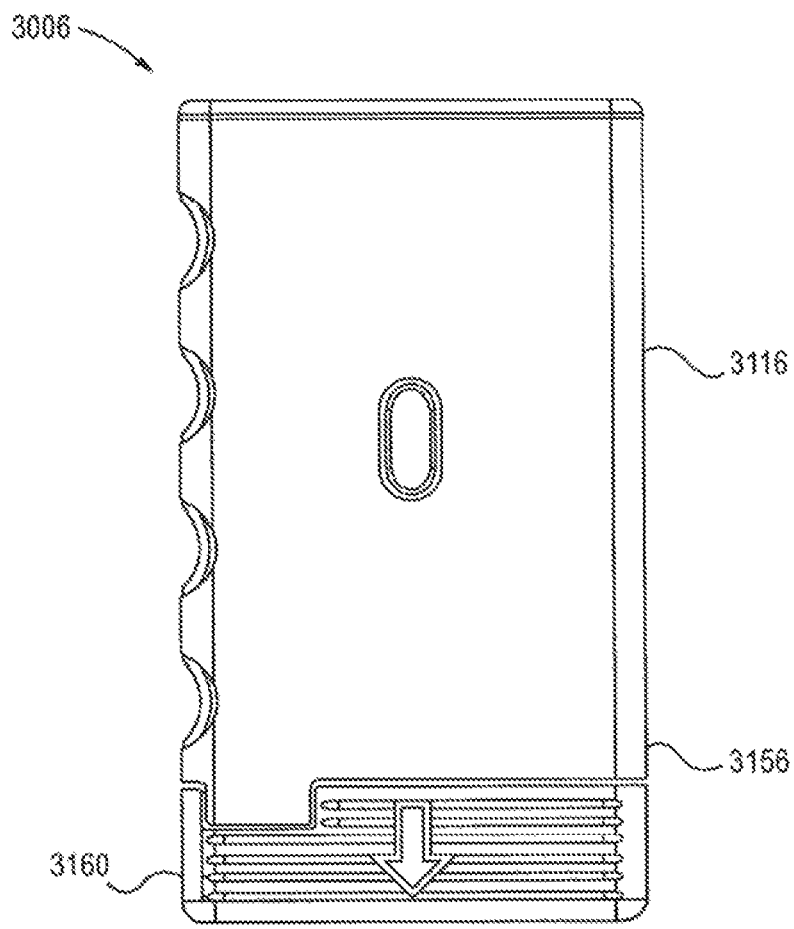
FIGS. 35-37 are front views of an auto-injector according to an embodiment of the invention in a first, second, and third configuration respectively.
Figure 36:
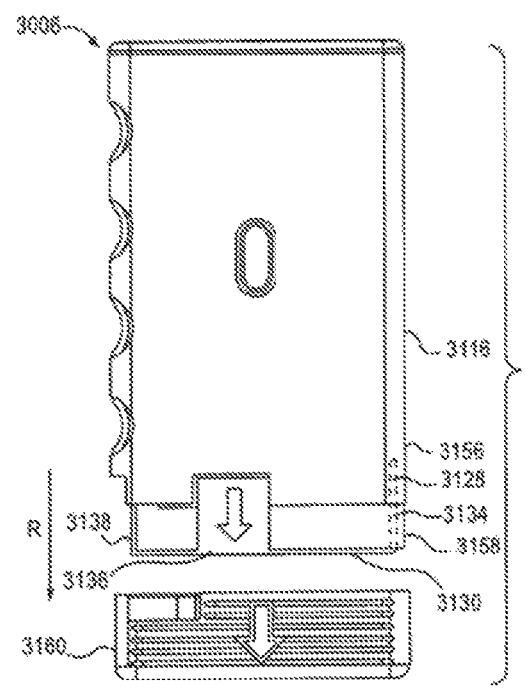
Figure 37:
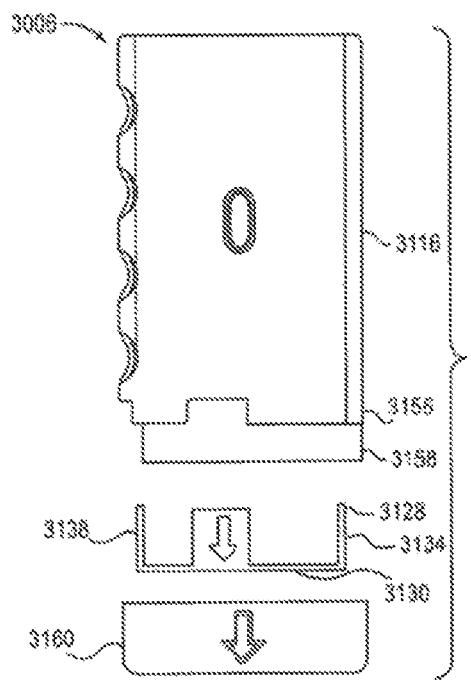

In some embodiments, as illustrated in FIGS. 35-37, an auto-injector 3006 includes a housing 3116, a safety guard 3130, and a distal end cap 3160. The distal end cap 3160 is configured to selectively engage or be coupled to the housing 3116. The distal end cap 3160 prevents inadvertent actuation of the auto-injector 3006 by substantially covering at least a portion of the safety guard 3130 when the distal end cap 3160 is engaged with or coupled to the housing 3116.

The distal end cap 3160 has a first position and a second position. In its first position, illustrated in FIG. 35, the distal end cap 3160 is removably coupled to or engaged with the distal end portion 3156 of the housing 3116. In its second position, illustrated in FIG. 36, the distal end cap 3160 is removed from the housing 3116. The distal end cap 3160 must be removed from the auto-injector 3006 before the auto-injector can be enabled for use, thus preventing inadvertent actuation of the device. Furthermore, the distal end cap 3160 provides an additional barrier to contamination of the needle and the medicament disposed therein. The distal end cap 3160 can have a series of ridges or other tactile mechanism for assisting a user in gripping and/or removing the distal end cap. The distal end cap 3160 is replaceable. As such, if the distal end cap 3160 is removed before a user intends to use the auto-injector 3006, the user can put the distal end cap back in its first position without actuating or jeopardizing the sterility of the device.

Figure 38:
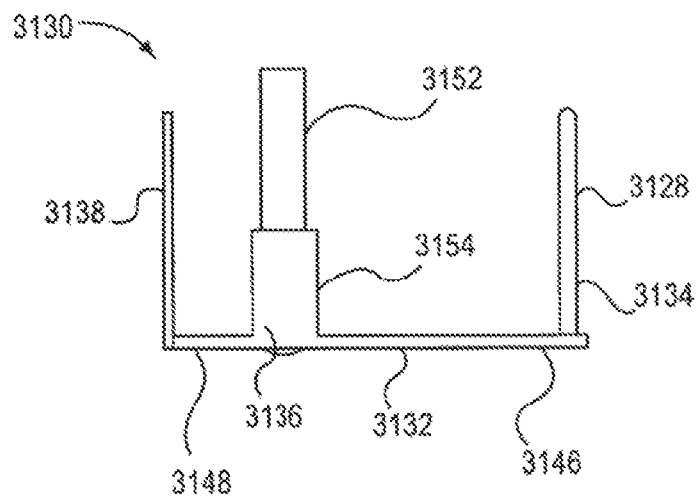
FIG. 38 is a front view of a portion of the auto-injector illustrated in FIGS. 36 and 37.
Figure 39:
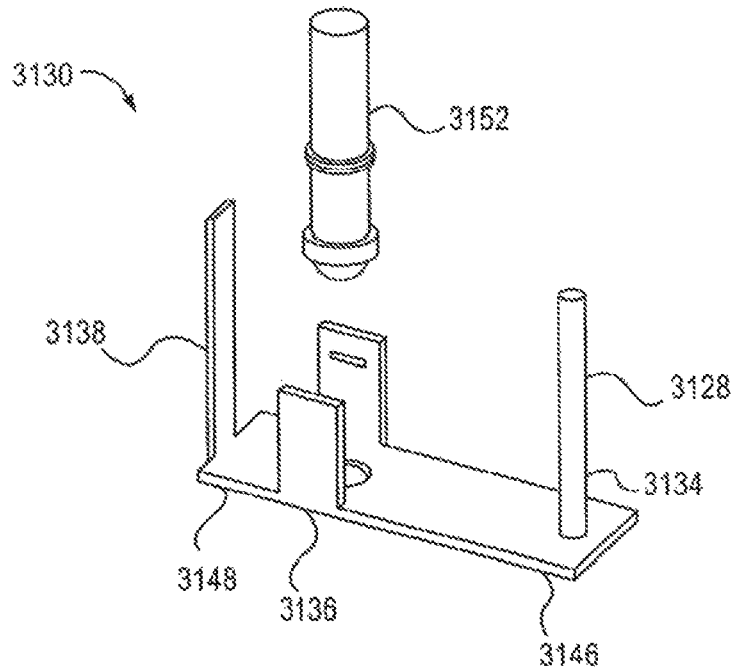
FIG. 39 is an exploded perspective view of the portion of the auto-injector illustrated in FIG. 38.

Once the distal end cap 3160 is removed, the safety guard 3130 is exposed and can be removed. With the safety guard 3130 in place, the auto-injector 3006 can not be actuated. The safety guard 3130, illustrated in FIGS. 38-39, includes a base portion 3132, a locking portion 3134, and a needle guard portion 3136. The locking portion 3134 and needle guard portion 3136 extend proximally from the base portion 3132. The base includes a first end 3146 and a second end 3148. The locking portion 3134 is disposed adjacent the first end 3146 and includes a first engagement portion 3128. A second engagement portion 3138 is disposed adjacent the second end 3148 of the base portion 3132.

The needle guard portion 3136 of the safety guard 3130 includes a sheath 3152 and a sheath retaining portion 3154. The sheath 3152, which is similar to sheath 3820 discussed in detail above, defines an opening configured to receive at least a portion of a needle of the auto-injector and is removably coupled to the sheath retaining portion 3154. The sheath retaining portion 3154 is couplable to the housing 3116 or to the base 3158 which is coupled to the housing.

The safety guard 3130 has a first position and a second position. In its first position, illustrated in FIG. 36, the safety guard 3130 is coupled to the distal end 3156 of the housing 3116. For example, the safety guard 3130 can be coupled to a base 3128 movably coupled to the distal end 3156 of the housing 3116. In its second position, shown in FIG. 37, the safety guard 3130 is removed from the housing 3116. The safety guard 3130 is removed from the housing 3116 by pulling the safety guard distally in the direction of arrow R.

When the safety guard 3130 is in its first position, the locking portion 3134 inhibits or prevents actuation of the auto-injector 3006. Referring to FIG. 36, the locking portion 3134 includes a first engagement portion 3128, or protrusion, that extends at least partially into the housing 3116 of the auto-injector 3006 (shown in dashed lines). In some embodiments, the locking portion 3134 extends through an opening (not shown in FIG. 36) of the base 3158 movably coupled to the distal end portion 3156 of the housing 3116, similar to the opening 3522 defined by base 3520 as illustrated in FIG. 14. The locking portion 3134 is configured to keep separate the projections of the actuator, similar to projections 3548 of actuator 3510 illustrated in FIG. 13, when the safety guard 3130 is in its first position. As the safety guard 3130 is moved from its first position to its second position, the locking portion 3134 is removed from between the projections 3548. Thus, the projections can be moved to actuate the auto-injector as previously described.

When the safety guard 3130 is in its first position, the needle guard portion 3136 substantially covers the needle (not shown) of the auto-injector 3006. As the safety guard 3130 is moved to its second position, the sheath retaining portion 3154 remains coupled to the sheath 3152, and thus sheath is removed from its position covering the needle.

The second engagement portion 3138 of the safety guard 3130 is configured to be selectively coupled to at least a portion of the housing 3116 when the safety guard 3130 is in its first position. The second engagement portion 3138, for example, can assist in guiding and removing the safety guard 3130 by balancing the safety guard relative to the housing 3116. In other words, as the safety guard 3130 is moved to its second (or removed) position, the second engagement portion 3138 inhibits the safety guard 3130 from becoming skewed, and restricting movement of the first engagement portion 3128. In some embodiments, the second engagement portion 3138 can be coupled to the housing 3116 to prevent unwanted movement of the safety guard 3130 away from the housing, such as via a resistance fit with the housing.

In some embodiments, the safety guard 3130 is constructed monolithically. In other embodiments, the safety guard can be constructed from separate components. For example, one or more of the base portion, locking portion and/or needle guard portion can be constructed separately and then coupled to the other portions. Although the illustrated embodiment shows the second engagement portion 3138 as being disposed at or proximate to an edge of the base portion 3132, in some embodiments, the second engagement portion 3138 can be disposed elsewhere on the base portion. Although the first engagement portion 3128, or locking member, is illustrated as being at or proximate to an edge of the base portion 3132, in some embodiments, the first engagement portion 3128 can extend from another portion of the base portion.

Figure 40:
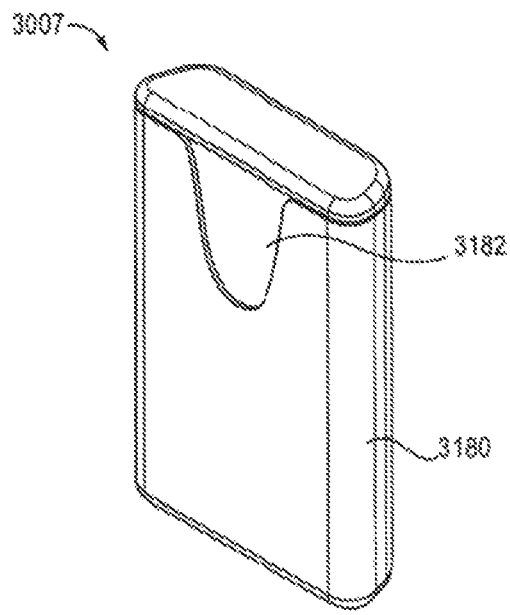
FIGS. 40 and 41 are perspective views of an auto-injector according to an embodiment of the invention in a first configuration and a second configuration respectively.
Figure 41:
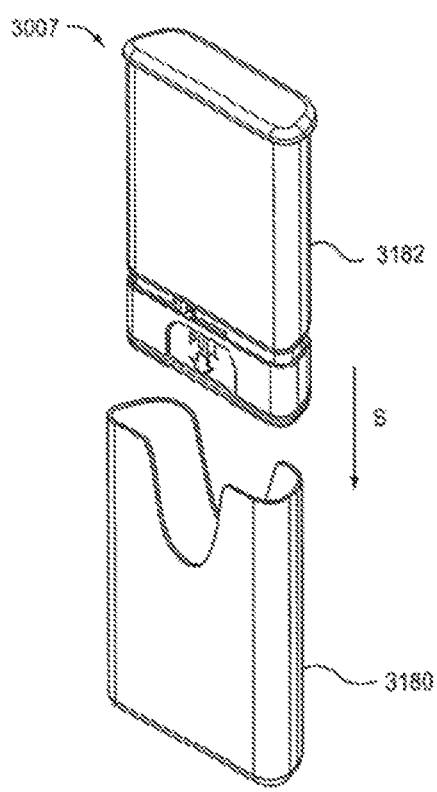

In some embodiments, a sleeve covers all or at least a substantial portion of the auto-injector. For example, as illustrated in FIG. 40, the sleeve 3180 covers substantially all of the safety guard (not shown) and the housing 3182 of the auto-injector 3007. The sleeve 3180 can be configured for use in an embodiment having only a safety lock or a separate needle guard and safety lock. The sleeve 3180 has a first position in which the sleeve is configured to substantially cover the housing 3182, as illustrated in FIG. 40, and a second position in which the sleeve is configured to be removed from the housing 3182 by pulling the sleeve distally in the direction of arrow S, as illustrated in FIG. 41.

Figure 42:
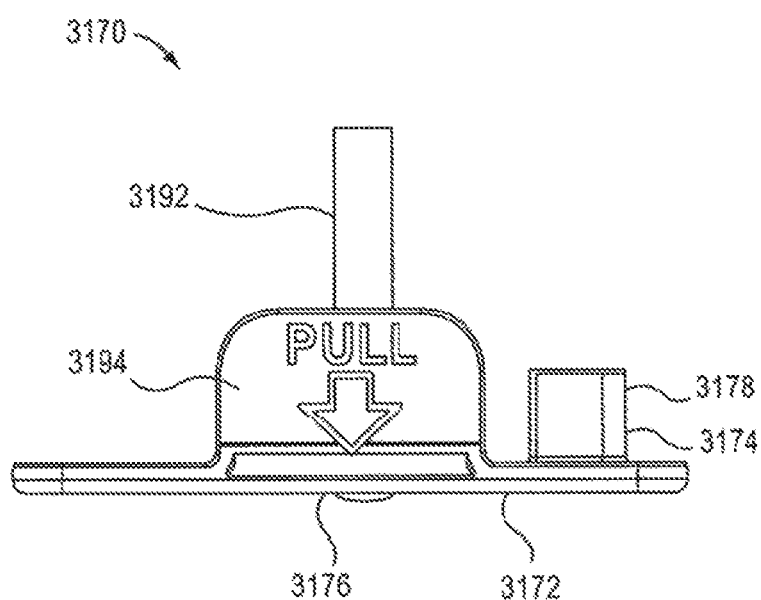
FIG. 42 is a front view of a portion of the auto-injector illustrated in FIG. 41.
Figure 43:
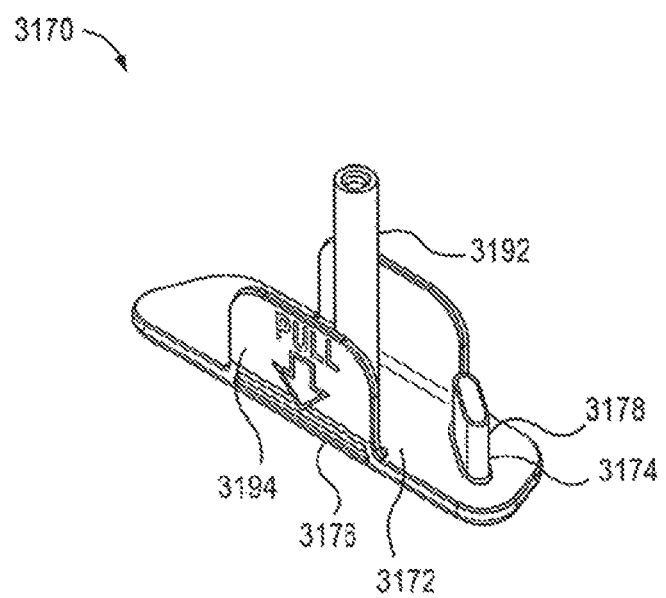
FIG. 43 is a perspective view of the portion of the auto-injector illustrated in FIG. 42.

Although the safety lock is described as having a first engagement portion and a second engagement portion, in some embodiments, the safety lock has only a first engagement portion. For example, as illustrated in FIGS. 42 and 43, a safety lock 3170 includes a locking portion 3174 and a needle guard portion 3176. The locking portion 3174 has a first engagement portion 3178 disposed on the base portion 3172 of the safety lock. The first engagement portion 3178 extends proximally from the base portion 3172. The needle guard portion 3176 includes a sheath 3192 and a sheath retaining portion 3194. The sheath retaining portion 3194 extends proximally from the base portion 3172 and is coupled to the sheath 3192. The sheath retaining portion 3194 is coupled to the sheath 3192 similar to the coupling of the sheath 3820 and sheath retainer 3840 as described in detail above with reference to FIG. 8. The safety lock 3170 is removed by pulling the safety lock distally in the direction of arrow S as shown in FIG. 41, away from housing 3182. When the safety lock 3170 is in its second (or removed) position, the first engagement portion 3178 is removed from between the projections of the system actuator rod (not shown in FIG. 41), and thus the auto-injector 3007 can be actuated.

In some embodiments, the locking member, distal end cap, safety guard, or sleeve are configured to mate or otherwise interface with the housing to prevent actuation of the auto-injector. The connection between the housing and the sleeve, for example, can be a snug fit and can be an interlocking connection. For example, in some embodiments, some force must be applied to remove the distal end cap, safety guard, or sleeve from the housing.

Figure 44:
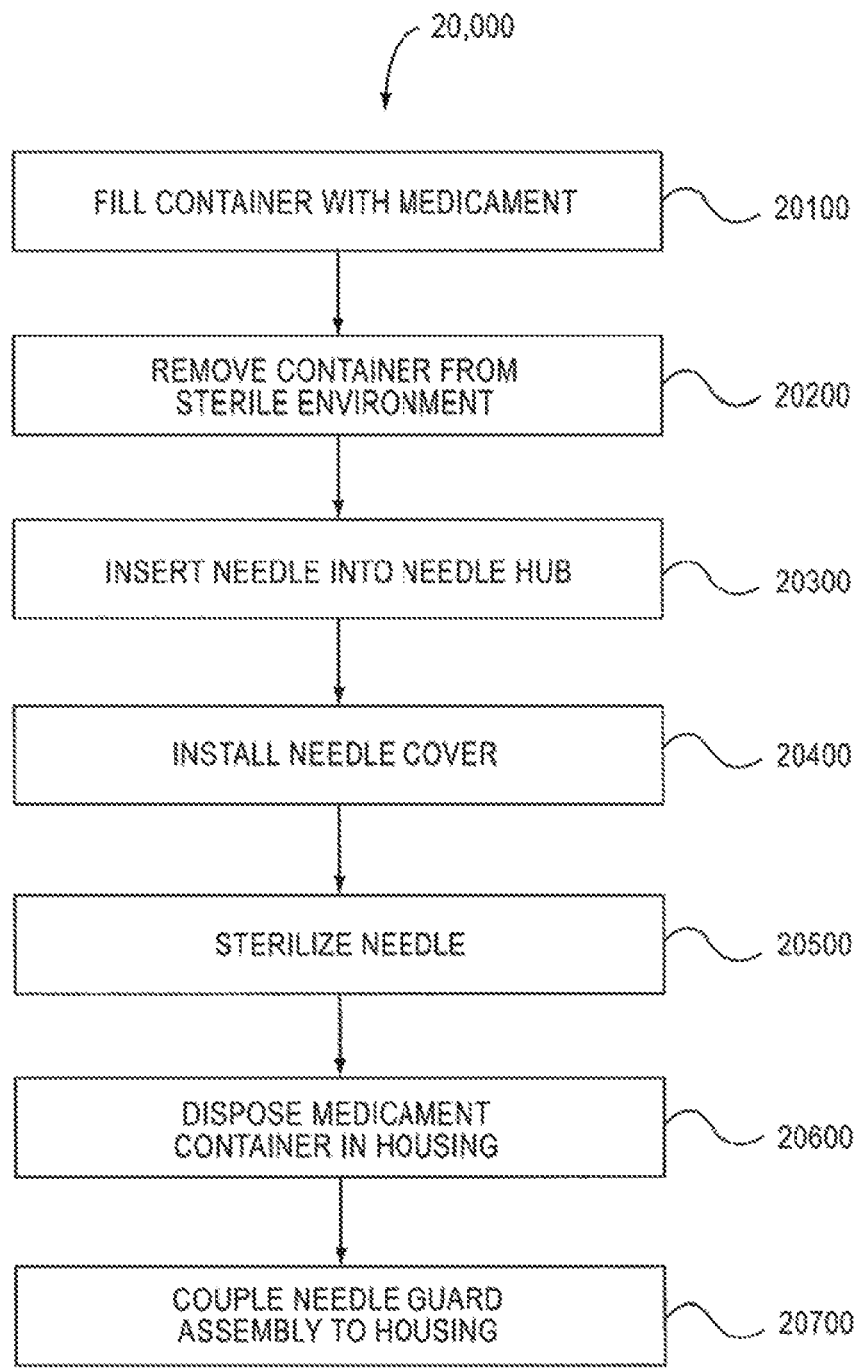
FIG. 44 is a flowchart illustrating a method according to an embodiment of the invention.

FIG. 44 is a flowchart of an embodiment of a method 10000 for manufacturing a medicament delivery apparatus. At 10010, a medicament container is filled with a predetermined amount of medicament. For example, the medicament container can be filled with a predetermined amount of epinephrine. As used herein, filling the medicament container includes putting medicament into the container, not necessarily filling the container to capacity. The filling of the medicament container occurs in a sterile environment. In some embodiments, the container can be filled with a second medicament. In such an embodiment, the second medicament can be any constituent of a medicament, including water. Once the medicament container is filled, a seal can be placed on the container to prevent leakage and/or contamination of the medicament. At activity 10020, the medicament container is removed from the sterile environment. For example, the medicament container can be filled in a first sterile manufacturing facility, and then the filled containers can be transported to a second facility, which is not necessarily a sterile facility, to continue assembly of the apparatus.

At 10030, at least a portion of a needle is inserted into a needle hub disposed in or on a housing. At 10040, a needle cover, or sheath, is installed over at least a portion of the needle so that the needle cover substantially covers the portion of the needle extending from the needle hub. For example, a needle cover constructed of at least one of polyethylene, high density polyethylene, polypropylene, polytetrafluoroethylene, thermoplastic polyurethane, rubber, a polymer, or an elastomer can be installed to cover at least a portion of the needle extending from the needle hub. When the needle cover is installed, the needle cover can also be coupled to the needle hub. For example, in some embodiments the needle cover includes a recessed portion configured to be coupled to a corresponding protrusion on the needle hub. In some embodiments, the recessed portion and the protrusion forms a seal that is resistant to microbial penetration. One or both of the insertion of the needle into the needle hub 10030 and installing the needle cover 10040 can occur in a non-sterile environment.

At 10050, the needle is sterilized. Various sterilization techniques may be utilized. In some embodiments, a suitable sterilization technique includes the use of one or more of ethylene oxide, gamma radiation, e-beam radiation, ultraviolet radiation, steam, plasma, or hydrogen peroxide. In some embodiments, the needle is sterilized prior to installing the needle cover. In some embodiments, the needle is sterilized after the needle cover is installed. For example, in some embodiments, the needle cover is installed and then a gas sterilant is conveyed through at least a portion of the needle cover. The needle is sterilized using a gas sterilization technique that can penetrate one or more pores of a porous needle cover. In some embodiments, the needle can be sterilized using a gas sterilization technique that can penetrate one or more pores of a porous needle cover, but that will not react with a medicament in a medicament container disposed in the housing.

In some embodiments, the gas sterilant is conveyed through a valve disposed on the needle cover. For example, the valve may be a one-way check valve, a spring-loaded valve, a self-sealing membrane, or the like.

At 10060, the medicament container is disposed in the housing. At 10070, a needle guard assembly is coupled to at least one of a distal end portion of the housing or an actuator (or base portion) coupled to the housing. In some embodiments, the coupling includes coupling a one piece safety guard that is configured to prevent actuation of the apparatus and to receive at least a portion of the needle cover. In some embodiments, the coupling includes first coupling an actuation guard, or locking member, configured to prevent actuation of the apparatus, and then coupling a needle guard configured to receive at least a portion of the needle cover and to prevent movement of the locking member when the needle guard is coupled to the housing or the base portion.

Although disposing the medicament container in the housing is illustrated and described as occurring after the needle cover is installed over at least a portion of the needle, in some embodiments, the medicament container is attached to the needle hub when the needle cover is installed over at least a portion of the needle.

Although only the needle is illustrated and described as being sterilized, in some embodiments, one or more of the needle hub, needle cover, and medicament container are sterilized in addition to the needle being sterilized. The sterilization of the needle hub, needle cover, medicament container and needle can occur substantially simultaneously or at different times.

Although the flowchart in FIG. 44 presents each activity for manufacturing an auto-injector in a particular order, the various activities can occur in a different order. For example, the medicament container can be filled with medicament after the needle has been sterilized. In another example, the medicament container can be disposed in the housing prior to inserting the portion of the needle into the needle hub.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although various embodiments have been described as having particular features and/or combinations of components, other embodiments are possible having a combination of any features and/or components from any of embodiments where appropriate. For example, in some embodiments, the sleeve 3180 illustrated in FIG. 40 can be used in connection with the auto-injector 3002, 3004, 3006. Additionally, any of the components of the needle guard and safety lock can be interchanged with similar components in similar embodiments.

What is claimed is:

1. An apparatus comprising:
a housing having a distal end portion;
a medicament container disposed within the housing;
a plunger having a distal end configured to move within the medicament container between a first position and a second position in response to a first force;
a needle coupled to the medicament container;
a needle sheath covering the needle; and
a sheath retainer configured to be disposed about at least a portion of the needle sheath, the sheath retainer including a grip surface configured to be manipulated by a user to move the sheath retainer distally relative to the housing, the sheath retainer including at least one retaining tab that engages the needle sheath and is configured to transfer a removal force to the needle sheath to remove the needle sheath from about the needle when the sheath retainer is moved distally; and
a case configured to contain at least the distal end portion of the housing, the case surrounding the needle when the distal end portion of the housing is within the case.

2. The apparatus of claim 1, wherein the needle sheath covering the needle is configured to maintain sterility of the needle.

3. The apparatus of claim 1, wherein the medicament container contains epinephrine.

4. The apparatus of claim 1, wherein the medicament container is configured to move within the housing, the apparatus further comprising:
a spring configured to urge the medicament container in a proximal direction.

5. The apparatus of claim 1, wherein the at least one retaining tab includes a plurality of tabs configured to exert the removal force against the needle sheath when the sheath retainer is moved distally relative to the housing to remove the needle sheath from the needle.

6. The apparatus of claim 1, wherein:
the housing is configured to be removed from within the case; and
the case limits distal movement of the sheath retainer when the housing is within the case.

7. The apparatus of claim 1, further comprising:
a pressurized gas container disposed within the housing, the pressurized gas container configured to produce a force when actuated; and
the pressurized gas container being operably coupled to the plunger such that the force is exerted on the plunger to cause a distal end of the plunger to move within the medicament container to expel a medicament.

8. The apparatus of claim 7, wherein:
the pressurized gas container includes a spring loaded check ball and gas release mechanism, and
the pressurized gas container is configured to release pressurized gas and produce the force when the spring loaded check ball is depressed.

9. The apparatus of claim 1, wherein:
the housing defines a status window;
a contents of the medicament container are viewable through the status window; and
the status window is covered by the case when the housing is disposed within the case.

10. The apparatus of claim 1, wherein an outer surface of the sheath retainer includes an indicium indicating an order of operation for removal of the sheath retainer.

11. The apparatus of claim 1, wherein the needle sheath includes an indicium indicating an order of operation for removal of the sheath retainer.

12. The apparatus of claim 1, further comprising:
an elastomeric member disposed within the medicament container; and
an actuator coupled to the housing, the actuator configured to move from a first actuator position to a second actuator position to produce the first force to move the elastomeric member within the medicament container to expel a medicament from within the medicament container via the needle.

13. The apparatus of claim 1, wherein the grip surface is configured to receive the removal force to move the sheath retainer in the distal direction relative to the housing.

14. The apparatus of claim 1, wherein:
an outer surface of the sheath retainer includes an indicium with a first arrow oriented in a direction of removal for the sheath retainer;
the needle sheath includes an indicium with a second arrow oriented in a direction of removal for the needle sheath; and
the orientation of the first arrow is different from the orientation of the second arrow.

\* \* \* \* \*